(12) United States Patent
Sweitzer

(10) Patent No.: US 11,839,386 B2
(45) Date of Patent: Dec. 12, 2023

(54) OSTEOTOME GUIDE

(71) Applicant: Shukla Medical, St. Petersburg, FL (US)

(72) Inventor: Zachary Robert Sweitzer, Keyport, NJ (US)

(73) Assignee: Shukla Medical, St. Petersburg, FL (US)

( * ) Notice: Subject to any disclaimer, the term of this patent is extended or adjusted under 35 U.S.C. 154(b) by 468 days.

(21) Appl. No.: 17/012,190

(22) Filed: Sep. 4, 2020

(65) Prior Publication Data

US 2021/0068851 A1     Mar. 11, 2021

Related U.S. Application Data

(60) Provisional application No. 62/897,251, filed on Sep. 6, 2019.

(51) Int. Cl.
*A61B 17/17* (2006.01)
*A61B 17/16* (2006.01)
*A61B 17/00* (2006.01)

(52) U.S. Cl.
CPC ...... *A61B 17/1735* (2013.01); *A61B 17/1604* (2013.01); *A61B 17/1613* (2013.01); *A61B 2017/00424* (2013.01)

(58) Field of Classification Search
CPC ............ A61B 17/1604; A61B 17/1732; A61B 17/1735
See application file for complete search history.

(56) References Cited

U.S. PATENT DOCUMENTS

| | | | | |
|---|---|---|---|---|
| 3,967,377 | A * | 7/1976 | Wells | F16H 25/20 33/813 |
| 5,409,493 | A * | 4/1995 | Greenberg | A61C 1/084 606/86 R |
| 6,679,886 | B2 * | 1/2004 | Weikel | A61B 17/7061 606/167 |
| 6,716,215 | B1 * | 4/2004 | David | A61B 17/1622 433/116 |
| 6,783,533 | B2 * | 8/2004 | Green | A61B 17/1617 606/80 |
| 6,863,677 | B2 * | 3/2005 | Breznock | A61B 17/320016 606/180 |
| 7,704,254 | B2 * | 4/2010 | Walen | A61B 17/142 606/82 |
| 10,874,406 | B2 * | 12/2020 | Laughlin | A61B 17/1631 |
| 11,096,698 | B2 * | 8/2021 | Bohl | A61B 17/17 |
| 2001/0037114 | A1 * | 11/2001 | Dinger | A61B 17/1688 606/171 |
| 2003/0040765 | A1 * | 2/2003 | Breznock | A61B 17/32053 606/184 |
| 2004/0092940 | A1 * | 5/2004 | Zwirnmann | A61B 17/1633 606/80 |
| 2005/0216019 | A1 * | 9/2005 | Eckman | A61B 17/320016 606/79 |

* cited by examiner

*Primary Examiner* — Anu Ramana
(74) *Attorney, Agent, or Firm* — Kim IP Law Group LLC

(57) ABSTRACT

An osteotome guide is provided. The osteotome guide includes a handle, a shaft within the handle and slidable to a selected longitudinal position with respect to the handle, a tool coupler attached to a distal end of the shaft for receiving a working tool, and a lock assembly to lock the shaft into the selected longitudinal position with respect to the handle.

23 Claims, 27 Drawing Sheets

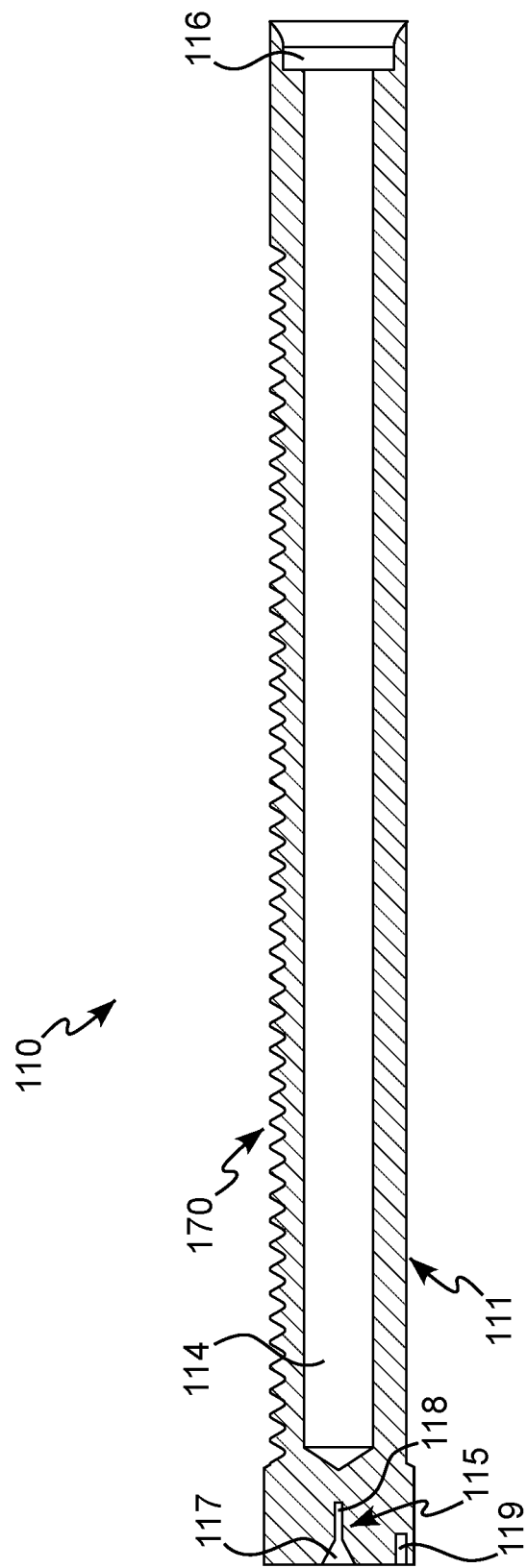

OSTEOTOME GUIDE

CROSS REFERENCE TO RELATED APPLICATIONS

The present application claims the benefit of U.S. Provisional Patent Application No. 62/897,251 filed Sep. 6, 2019 entitled "Osteotome Guide," the entire disclosure of which is hereby incorporated herein by reference.

BACKGROUND OF THE INVENTION

Exemplary embodiments of the subject disclosure relate generally to tools used in medical procedures, and more specifically, to osteotome guides.

Conventional osteotomes are simple chisel-like devices used for cutting or preparing bone. Generally, osteotomes do not allow for adjustment of blade length or operation in multiple modes that would be advantageous to a user, e.g., a surgeon.

BRIEF SUMMARY OF THE INVENTION

In accordance with one embodiment of the subject disclosure, an osteotome guide is provided. The osteotome guide includes a handle; a shaft within the handle and slidable to a selected longitudinal position with respect to the handle; a tool coupler attached to a distal end of the shaft for receiving a working tool; and a lock assembly to lock the shaft into the selected longitudinal position with respect to the handle.

In accordance with one aspect of the subject disclosure, the handle includes a central longitudinal bore.

In accordance with another aspect of the subject disclosure, the handle includes screw threads about its distal end for coupling to a threaded collar.

In accordance with still another aspect of the subject disclosure, the shaft is elongated.

In accordance with yet another aspect of the subject disclosure, the shaft includes a plurality of grooves.

In accordance with still another aspect of the subject disclosure, the shaft includes a distal end having a shaft slot for receiving the working tool.

In accordance with yet another aspect of the subject disclosure, the tool coupler includes a tool guide having an internal cavity and a clasp positioned within the internal cavity.

In accordance with still another aspect of the subject disclosure, the clasp is positionable between a clasped position and an unclasped position.

In accordance with yet another aspect of the subject disclosure, the tool coupler further includes a biasing member to bias the clasp into the clasped position.

In accordance with still another aspect of the subject disclosure, the lock assembly comprises: a housing; and a clamp mounted within and moveable relative to the housing between a clamped position and an unclamped position, wherein in the clamped position the clamp engages the shaft to lock the shaft into the selected longitudinal position.

In accordance with yet another aspect of the subject disclosure, the clamp includes an inner locking surface for engaging the shaft when the clamp is in the clamped position.

In accordance with still another aspect of the subject disclosure, the inner locking surface of the clamp includes a plurality of locking ribs.

In accordance with yet another aspect of the subject disclosure, the clamp includes a biasing member to bias the clamp into the unclamped position.

In accordance with still another aspect of the subject disclosure, the lock assembly further includes a collar circumscribing the housing and rotatable about the housing between locked and unlocked positions, and the collar maintains the clamp in the clamped position when the collar is positioned into the locked position.

In accordance with yet another aspect of the subject disclosure, the clamp further includes a button extending past the collar and being manually manipulatable to urge the clamp into the clamped position.

In accordance with still another aspect of the subject disclosure, the osteotome guide further includes a securing coupler connected to a proximal end of the shaft for coupling to an object.

In accordance with yet another aspect of the subject disclosure, the osteotome guide further includes a nozzle coupled to the handle.

In accordance with still another aspect of the subject disclosure, the nozzle includes a slit for receiving the working tool.

In accordance with yet another aspect of the subject disclosure, the osteotome guide further includes a threaded collar structured to couple the nozzle to the handle.

In accordance with another embodiment of the subject disclosure, an osteotome guide is provided. The osteotome guide includes a handle having a longitudinal bore; a guide shaft having a distal end, a proximal end, and an outer surface provided with a plurality of grooves; the guide shaft disposed within the bore of the handle and slidable to a selected longitudinal position with respect to the handle; a tool coupler attached to the distal end of the guide shaft to removably receive the osteotome blade, the tool coupler including a clasp positionable into a locked position to lock the osteotome blade to the guide shaft and an unlocked position to unlock the osteotome blade from the guide shaft and a biasing member biasing the clasp into the locked position; a tapered nozzle having a slit for receiving the osteotome blade and an inner surface provided with a detent, the nozzle coupled to a distal end of the handle and engageable with the clasp of the tool coupler when the shaft is positioned into an overextended position; a lock assembly including: a housing having; a clamp positioned within the housing and having a stopping surface, an outside surface, a button adjacent to the outside surface and an internal clamping surface provided with a plurality of locking ribs, the clamp being positionable into a clamped position and an unclamped position, the locking ribs engaging the grooves of the guide shaft in the clamped position to lock the guide shaft into the selected longitudinal position, the button being manually manipulatable to urge the clamp into the clamped position, a toggle spring to bias the clamp into the unclamped position, a collar circumscribing the clamp and having an inner surface, the collar being rotatable into a closed position and an open position, the inner surface of the collar maintaining the clamp in the clamped position when the collar is rotated into the closed position, the stopping surface of the clamp engaging with the collar when the clamp is in the unclamped position to prevent the collar from being rotated from the open position to the closed position, and a torsion spring to bias the collar into the closed position; and a securing coupler connected to the proximal end of the guide shaft to couple the guide shaft to an object.

In accordance with still another embodiment of the subject disclosure, a method of operating an osteotome guide is provided. The method includes attaching a working tool to a tool coupler; retracting the working tool into a handle; and striking a securing coupler to advance the working tool into a bone without first operating a lock assembly to lock a shaft into a selected longitudinal position with respect to the handle.

In accordance with yet another embodiment of the subject disclosure, a method of operating an osteotome guide is provided. The method includes attaching a working tool to a tool coupler; positioning a shaft into a selected longitudinal position with respect to a handle, thereby positioning the working tool to a desired position with respect to a nozzle; operating a lock assembly to lock the shaft into the selected longitudinal position with respect to the handle; and striking a securing coupler to advance the working tool into a bone until the nozzle contacts the bone.

BRIEF DESCRIPTION OF THE SEVERAL VIEWS OF THE DRAWINGS

The following detailed description of an exemplary embodiment of the subject disclosure will be better understood when read in conjunction with the appended drawings. For the purpose of illustrating the present disclosure, there is shown in the drawings an exemplary embodiment. It should be understood, however, that the subject application is not limited to the precise arrangements and instrumentalities shown.

FIG. 3 is a side cross-sectional view of a shaft of the osteotome guide of FIG. 1A;

DETAILED DESCRIPTION OF THE INVENTION

Figure 1A:
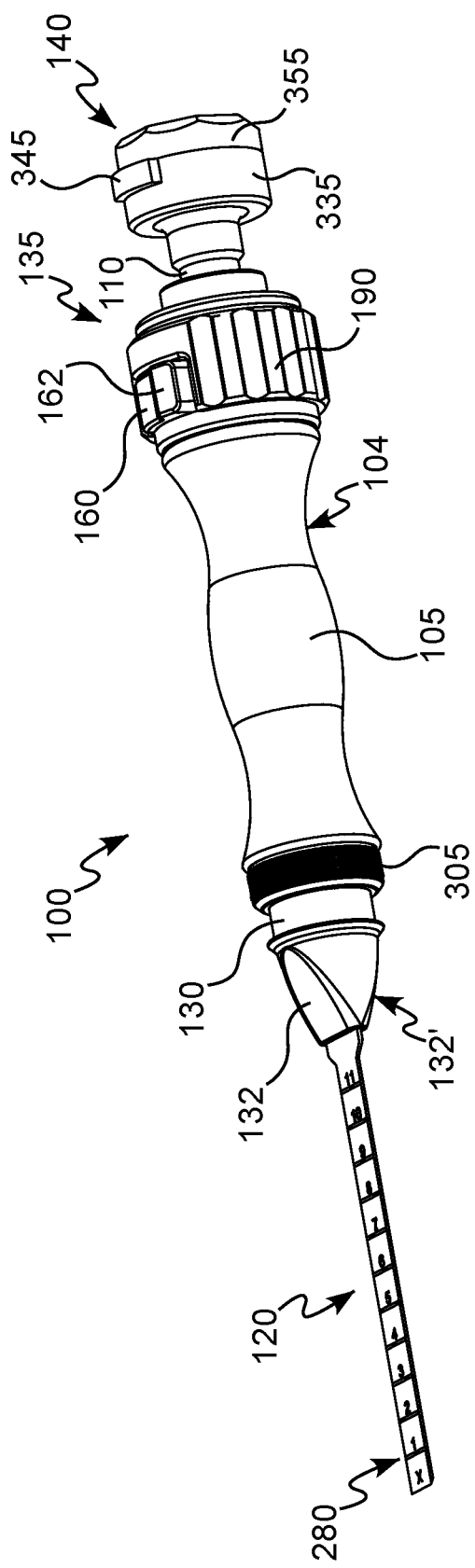
FIG. 1A is a perspective view of an osteotome guide with an installed working tool, in accordance with an embodiment of the subject disclosure.

Reference will now be made in detail to an exemplary embodiment of the subject disclosure illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as upper, lower, top, bottom, above, below and diagonal, are used with respect to the accompanying drawings. Such directional terms used in conjunction with the following description of the drawings should not be construed to limit the scope of the subject disclosure in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

"Substantially" as used herein shall mean considerable in extent, largely but not wholly that which is specified, or an appropriate variation therefrom as is acceptable within the field of art.

"Exemplary" as used herein shall mean "example" and is not intended to identify any embodiment or structure as preferred or more desirable than any other.

Throughout the subject application, various aspects thereof can be presented in a range format. It should be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments of the subject disclosure may be combined in any suitable manner in one or more embodiments. One skilled in the relevant art will recognize, in light of the description herein, that the subject disclosure can be practiced without one or more of the specific features or advantages of a particular exemplary embodiment. In other instances, additional features and advantages may be recognized in certain embodiments that may not be present in all exemplary embodiments of the present disclosure.

Referring now to the Figures, there is shown an exemplary embodiment of an osteotome guide 100 in accordance with the subject disclosure. As best shown in FIGS. 1A through 1D, the osteotome guide 100 includes a handle 105, a shaft 110 positioned slidably within the handle 105, a tool coupler 125 attached distally to the shaft 110 for removably receiving and locking a working tool 120, a nozzle 130 coupled to the distal end of the handle 105, a lock assembly 135 coupled to the proximal end of the handle 105 to lock the shaft 110 into a selected longitudinal position with respect to the handle 105, and a securing coupler 140 attached to the proximal end of the shaft 110 for removably coupling the osteotome guide 100 to an object, such as a handle or the like. As more fully described below, the osteotome guide 110 is operable to permit a user to adjust and lock the working tool 120 into a desired position relative to the osteotome guide 100 in accordance with requirements of a specific medical procedure.

Figure 1B:
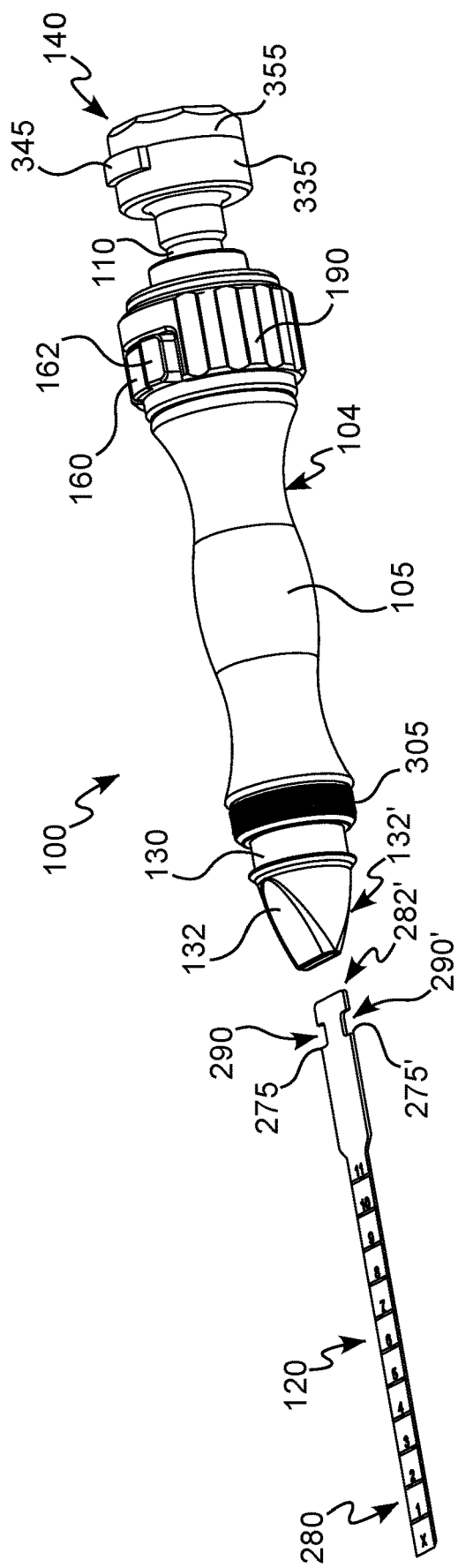
FIG. 1B is a perspective view of the osteotome guide of FIG. 1A with the working tool removed.

As best shown in FIGS. 1A and 1B, the working tool 120 is an osteotome blade, although it should be appreciated that the working tool 120 may include other tools or bits for performing any of various medical procedures. The working tool 120 includes a distal working end 280 and a proximal attachment end 282 having two locking slots 290, 290' with respective locking edges 275, 275' for removably coupling the working tool 120 to the osteotome guide 100. It should be appreciated that the proximal attachment end 282 may be provided with coupling structures in addition to or in lieu of locking slots 290, 290', and that various embodiments of the subject disclosure are not intended to be limited to any particular number or type of coupling structure(s) for coupling the working tool 120 to the osteotome guide 100.

The working tool 120 is also provided with a plurality of depth markers used to measure a dispensing depth of the working tool 120 relative to the osteotome guide 100. Though not necessary, the most distal flat edge of the nozzle 130 may be used as an indicator to identify the marker associated with the selected depth of the working tool 120. In the embodiment depicted in the Figures, the working tool 120 includes 11 depth markers (1-11), though it should be appreciated that any number of markers may be provided and that each marker may be designated using different reference designations, such as, for example, letters, symbols, a combination of the aforementioned, etc. It should also be appreciated that depth markers (not shown) may be provided at the proximal end of shaft 110 in addition to or in lieu of those on the working tool 120, in which case the most proximally facing face of the threaded cap 210 of lock assembly 135 may be used (but need not be used) as an indicator to identify the marker associated with the selected depth of the working tool 120.

Figure 1C:
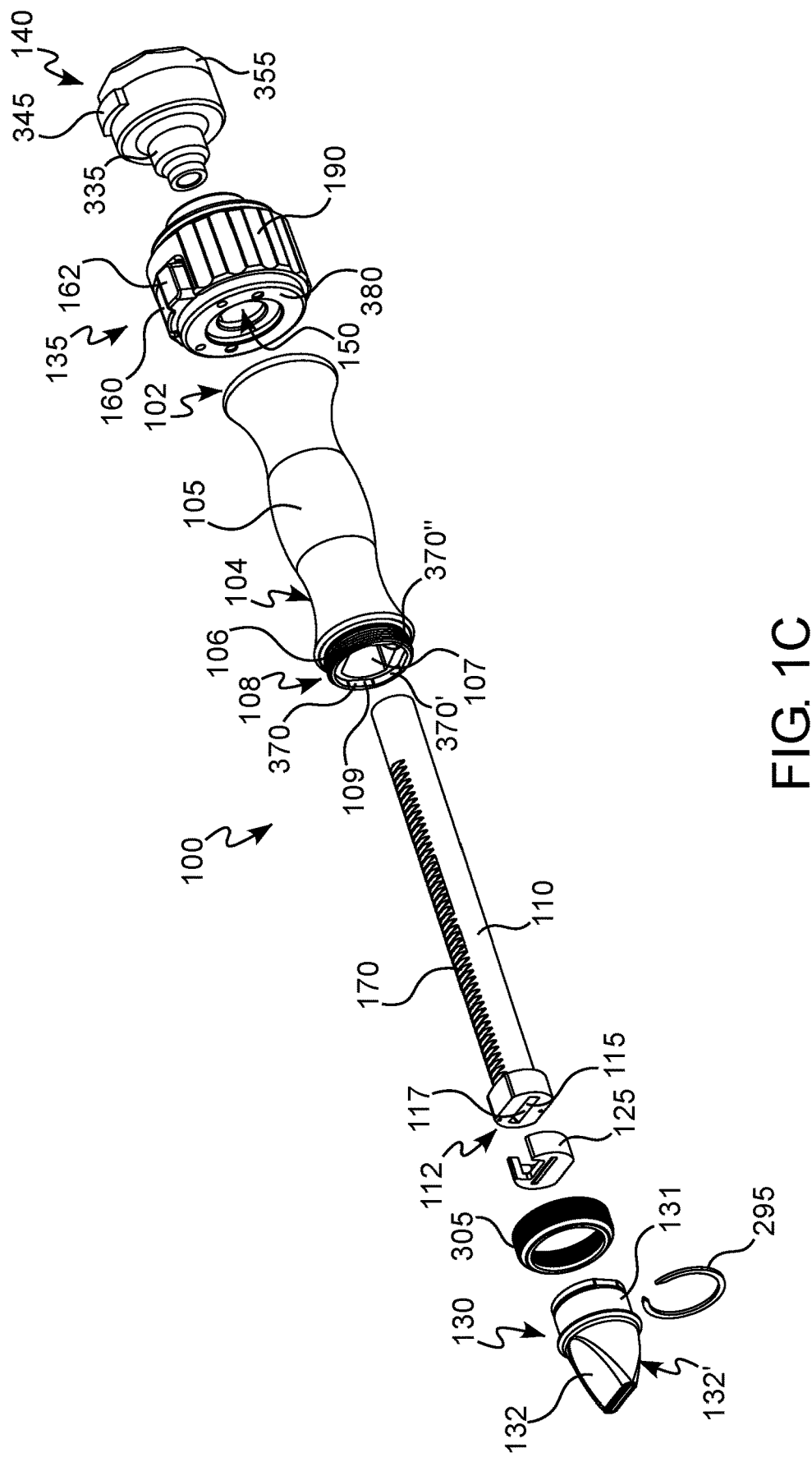
FIG. 1C is an exploded perspective view of the osteotome guide of FIG. 1A.
Figure 1D:
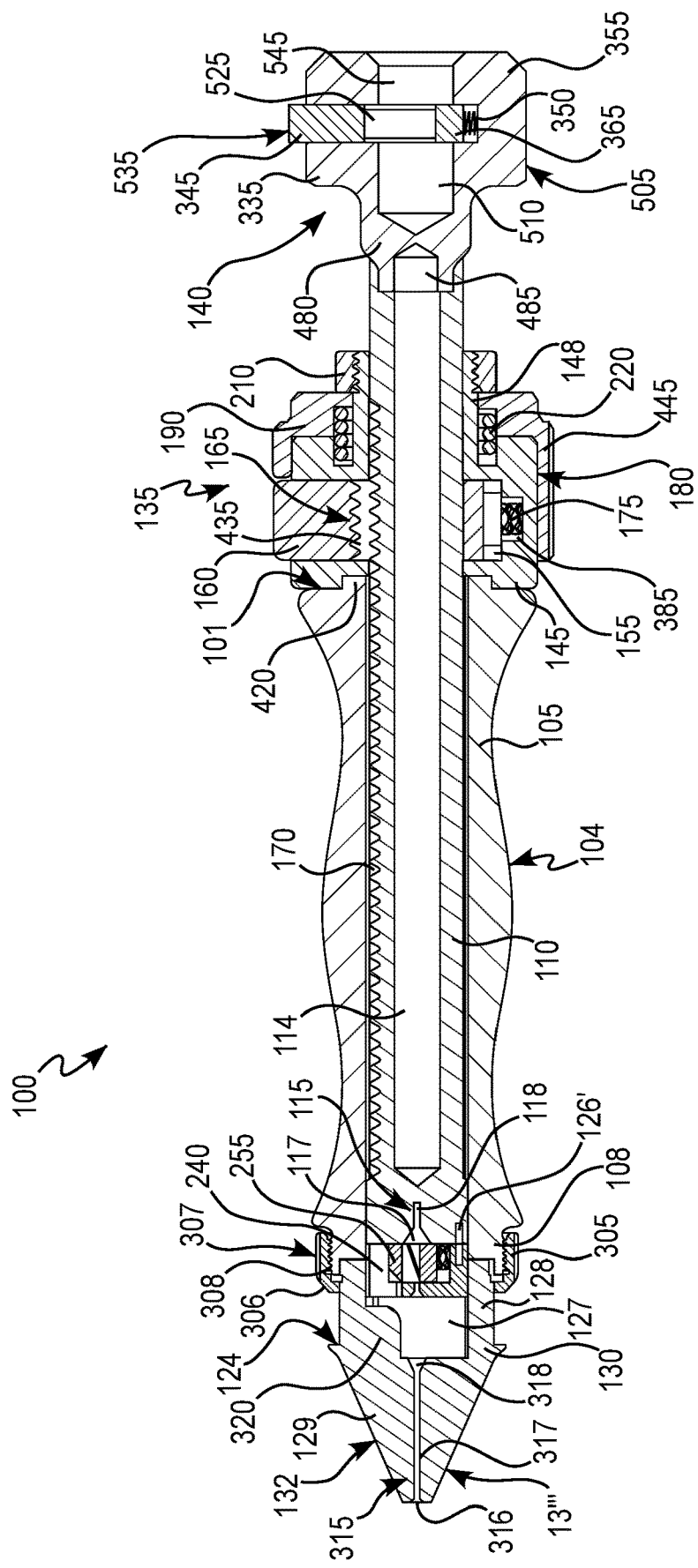
FIG. 1D is a side cross-sectional view of the osteotome guide of FIG. 1A.
Figure 2:
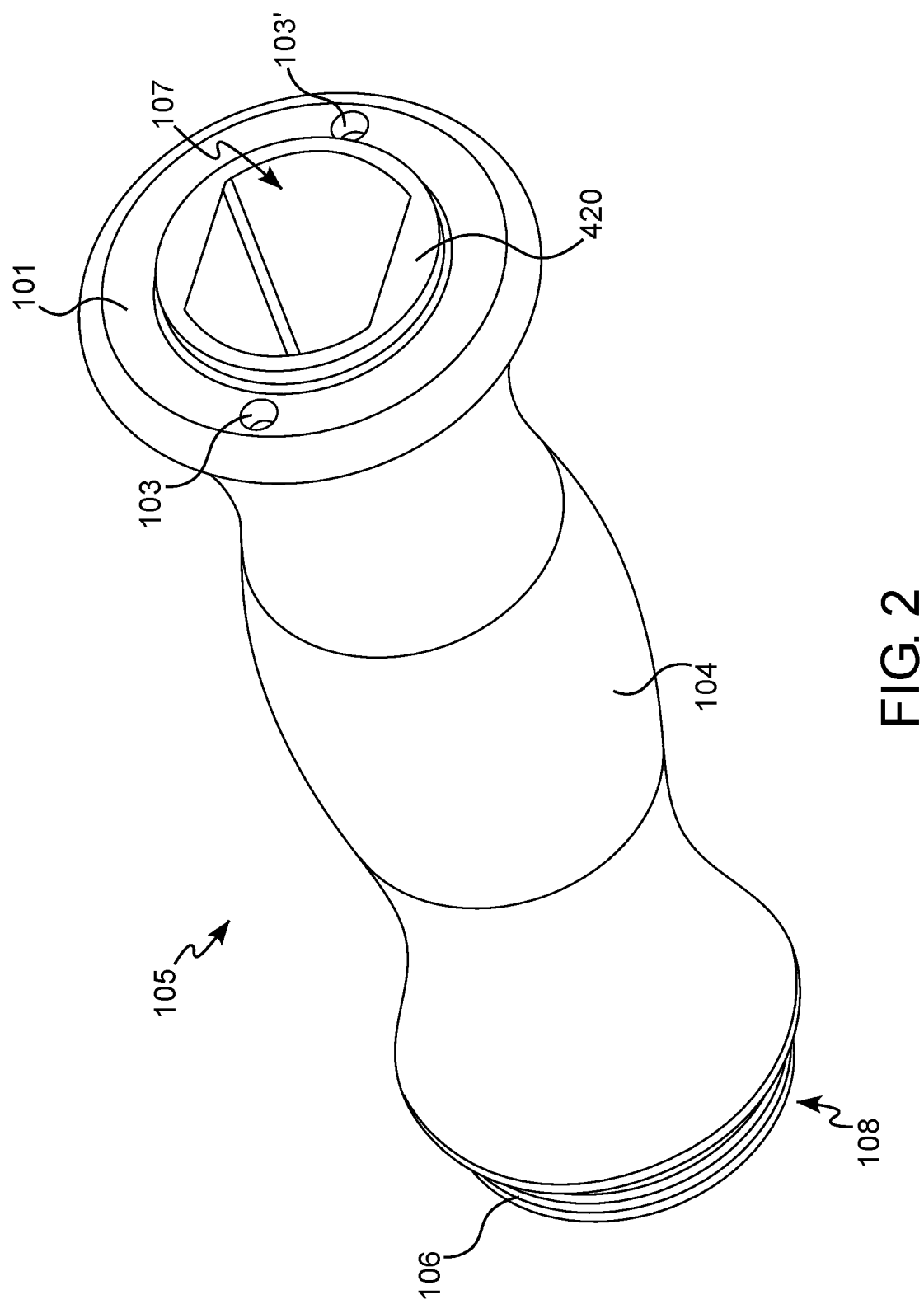
FIG. 2 is a perspective view of a handle of the osteotome guide of FIG. 1A.

As best shown in FIGS. 1C, 1D, and 2, the handle 105 is elongated to accommodate the hand of a user and includes an outside surface 104, a cylindrically-shaped distal end 108 recessed from the outside surface 104 and having an internal pocket 109 with keyed surfaces 370, 370', 370" for accommodating the nozzle 130 (see below) and screw threads 106 disposed externally thereon, and a longitudinal bore 107 extending through the entire length of the handle 105. The handle 105 also includes a proximal end having an alignment member 420 extending circumferentially about the longitudinal bore 107 and a proximally facing annular ledge 101 provided with two fastening holes 103, 103' for coupling the handle 105 to the lock assembly 135, though it should be appreciated that any number of fastening holes may be provided. It should also be appreciated that the fastening holes 103, 103' may be replaced by or supplemented with other structures for coupling the handle 105 to the lock assembly 135, and that various embodiments of the subject disclosure are not intended to be limited to any particular number or type of structure(s) for doing so.

The outside surface 104 of the handle 105 has an hourglass shape for ergonomic gripping by a user, though it should be appreciated that the handle 105 may be constructed to exhibit different shapes, such as, for example, a cylindrical shape. It should also be appreciated that the handle 105 may be provided with other features to improve ergonomic gripping, such as, for example, stippling, texturing, finger grooves, a polymer coating, etc.

The longitudinal bore 107 of the handle 105 is shaped to slidably receive the shaft 110. In the embodiment depicted in the Figures, for example, the longitudinal bore 107 has a cross-section approximately matching that of a distal portion of the shaft 110 and resembling a rectangle with two opposite rounded sides, though it should be appreciated that the cross-section of the longitudinal bore 107 may exhibit any shape, such as, for example, a circle, a square, a rectangle, a triangle, etc. It should also be appreciated that the cross-section of the longitudinal bore 107 need not approximately match the cross-section of the shaft 110.

As best shown in FIGS. 1C, 1D, 3, 5, and 7C, the shaft 110 includes a distal end provided with a shaft slot 115 for receiving the working tool 120 and fastening holes, e.g., two fastening holes 119, 119', for coupling the shaft 110 to the tool coupler 125, a blind longitudinal bore 114 extending distally from the proximal end of the shaft 110, and an outer surface provided with locking grooves 170 positioned to engage with the lock assembly 135 to lock the shaft 110 into a selected longitudinal position with respect to the handle 105. The shaft 110 also includes an internal annular pocket 116 at its proximal end for coupling the shaft 110 to the securing coupler 140. The annular pocket 116 has a diameter greater than that of the longitudinal bore 114 and an inner surface that curves radially toward the outer surface of the shaft 110 in the proximal direction, though it should be appreciated that the annual pocket 116 may exhibit any suitable shape and/or dimensions for coupling the shaft 110 to the securing coupler 140. It should also be appreciated that the shaft 110 may be provided with structures in addition to or in lieu of the annular pocket 116 for coupling the shaft 110 to the securing coupler 140, and that various embodiments of the subject disclosure are not intended to be limited to any specific number or type of structure(s) for doing so.

The distal end of the shaft 110 has a cross-section similar to that of the longitudinal bore 107 of the handle 105 and, in this manner, acts to controllably guide sliding of the shaft 110 within the longitudinal bore 107. The remaining length of the shaft 110 has a circular cross-section, though it should be appreciated that the remaining length of the shaft 110 may be provided with alternatively shaped cross-sections. In one embodiment, the shaft 110 exhibits a single cross-section extending along the entire length of the shaft 110.

The locking grooves 170 are provided on a lateral side of the shaft 110 along approximately the entire longitudinal length of the shaft 110, with each locking groove 170 extending partially around the shaft 110 in a circumferential direction. It should be appreciated that the shaft 110 may be provided with any number of locking grooves 170 of any size and length, and that each groove 170 may have a cross-section of any suitable shape, such as, for example, a V-shaped cross section, a U-shaped cross section, etc. It should also be appreciated that the locking grooves 170 may be replaced by or supplemented with other structures for locking the shaft 110 into the selected longitudinal position, and that various embodiments of the subject disclosure are not intended to be limited to any specific number or type of locking structure(s).

The shaft slot 115 is provided at the distal end of the shaft 110 and faces distally toward the nozzle 130. The shaft slot 115 has a width substantially greater than its height and includes an enlarged front opening 117 that tapers proximally and inwardly toward a smaller receipt opening 118 having a height approximately equal to that of the proximal attachment end 282 of the working tool 120.

Referring now to FIGS. 5 through 7C, the tool coupler 125 is operable to removably receive and lock the working tool 120. The tool coupler 125 includes a tool guide 240, a clasp 255 slidably positioned within the tool guide 240, biasing members 260, 260' positioned within the tool guide 240 and engaging the clasp 255, and fasteners 126, 126' for coupling the tool guide 240 to the distal end of the shaft 110.

The tool guide 240 includes a proximal end having an open internal cavity 250, a distally facing guide slot 245 terminating proximally at the internal cavity 250, a front-side cutout 252 extending along the entire longitudinal length of the tool guide 240 and communicating with the internal cavity 250, and proximally facing fastening holes, e.g., two fastening holes 254, 254', for coupling the tool guide 240 to the distal end of the shaft 110, though it should be appreciated that any number of fastening holes may be provided. It should also be appreciated that the fastening holes 254, 254' may be replaced by or supplemented with other structures for coupling the tool guide 240 to the shaft 110, and that various embodiments of the subject disclosure are not intended to be limited to any particular number or type of structure(s) for doing so.

Similar to the shaft slot 115 of the shaft 110, the guide slot 245 of the tool guide 240 has a width substantially greater than its height and includes an enlarged front opening 246 that tapers proximally and inwardly toward a smaller receipt opening 247. The opening 247 has a height approximately equal to that of the proximal attachment end 282 of the working tool 120 to allow the opening 247 to slidably accommodate the working tool 120.

The open internal cavity 250 of the tool guide 240 is shaped to slidably receive the clasp 255. In the embodiment shown in the Figures, for example, the internal cavity 250 has rounded lateral sides and a width approximately equal to (but slightly larger than) the width of the clasp 255. The internal cavity 250 also has a height greater than that of the clasp 255 to permit the clasp 255 to slide freely within the internal cavity 250. The rear side of the internal cavity 250 is provided with side-by-side receptacles 249, 249' for respectively receiving and maintaining the biasing members 260, 260'.

The fasteners 126, 126' of the tool coupler 125 are structured to engage with the fastening holes 119, 119' of the shaft 110 and the fastening holes 254, 254' of the tool guide 240 to secure the tool guide 240 to the distal end of the shaft 110, thereby closing the internal cavity 250 of the tool guide 240 and ensuring that the clasp 255 does not escape therefrom. In the embodiment depicted in the Figures, the fasteners 126, 126' are fastening pins, e.g., press-fit fastening pins, though it should be appreciated that different fasteners may be employed, such as, for example, screws, bolts, clips, etc. It should also be appreciated that the fasteners 126, 126' may be replaced by or supplemented with other structures for securing the tool guide 240 to the shaft 110, and that various embodiments of the subject disclosure are not intended to be limited to any particular number or type of structure(s) for doing so.

The clasp 255 of the tool coupler 125 includes a front surface 330, a longitudinally extending through-hole 265, an inside surface 285 adjacent a rear side of the through-hole 265, and locking elements 270, 270' with respective ramped surfaces 310, 310' positioned on the inside surface 285 at opposite sides of the through-hole 265. The ramped surfaces 310, 310' of the locking elements 270, 270' ramp upwardly in a proximal direction toward the front of the through-hole 265 such that a cross section of the through-hole 265 exhibits a T-shape at the proximal end of the clasp 255. The clasp 255 is slidable within the internal cavity 250 of the tool guide 240 from a clasped position, at which the locking elements 270, 270' respectively engage the locking edges 275, 275' of the working tool 120 to lock the tool 120 to the tool coupler 125 (see FIGS. 7B, 7C and 16A), and an unclasped position, at which the locking elements 270, 270' disengage the edges 275, 275' to permit free removal of the working tool 120 from the tool coupler 125 (see FIGS. 7A, 16B and 16C).

The front surface 330 of the clasp 255 extends upwardly through the front-side cutout 252 of the tool guide 240 and is provided with a distally facing sloped camming portion 258 for engaging with a cam protrusion 320 of the nozzle 130 in a manner more fully described below. The rear surface of the clasp 255 is provided with side-by-side and longitudinally extending receipt grooves 257, 257' for respectively receiving fronts of the biasing members 260, 260', though other structures may be provided on the clasp 255 for receiving the biasing members 260, 260'.

The biasing members 260, 260' are positioned within the receptacles 249, 249' of the internal cavity 250 and engage respectively with the longitudinal receipt grooves 257, 257' of the clasp 255 to bias the clasp 255 into the clasped position. In the embodiment depicted in the Figures, the biasing members 260, 260' are springs. It should be appreciated that the biasing members 260, 260' may be replaced by or supplemented with other structures for biasing the clasp 255 into the clasped position, and that various embodiments of the subject disclosure are not intended to be limited to any specific number or type of biasing structures.

Figure 4A:
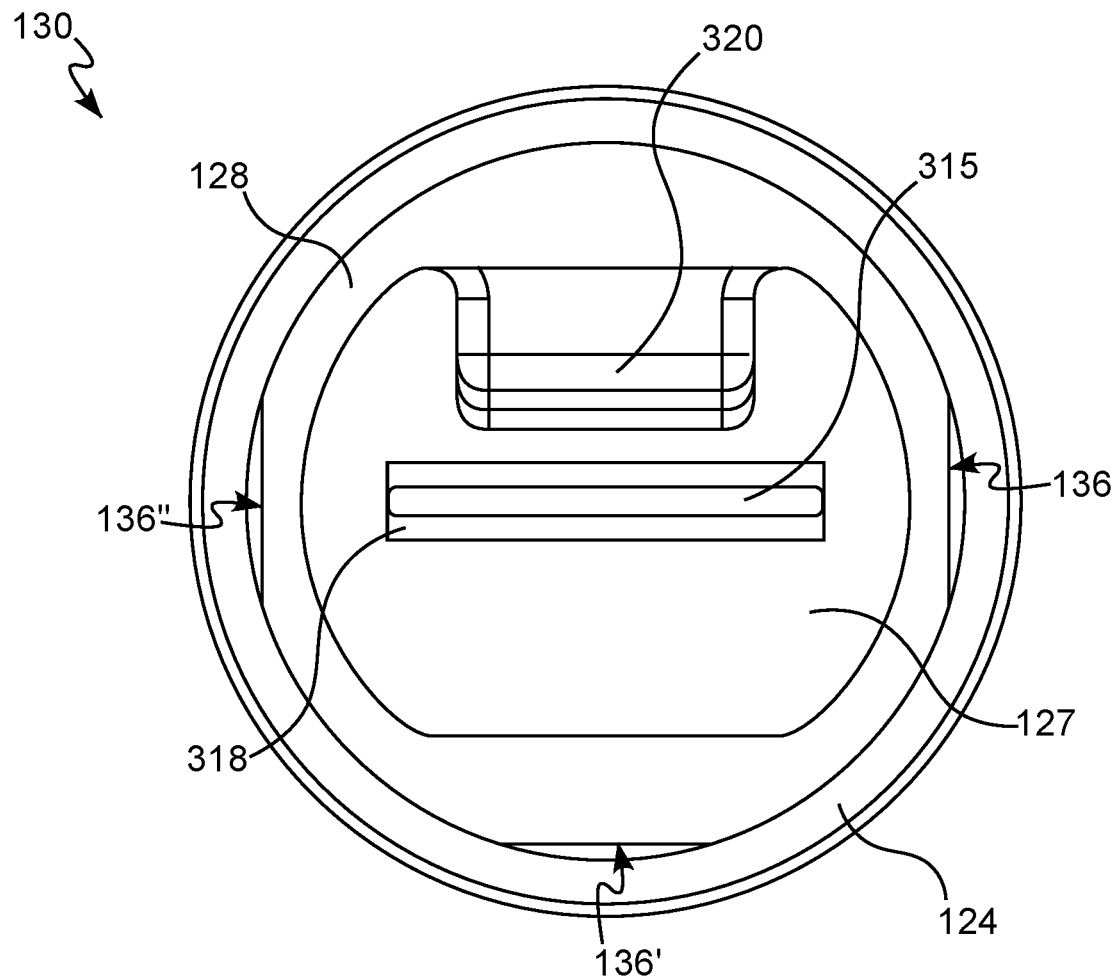
FIG. 4A is a distally facing side view of a nozzle of the osteotome guide of FIG. 1A.
Figure 4B:
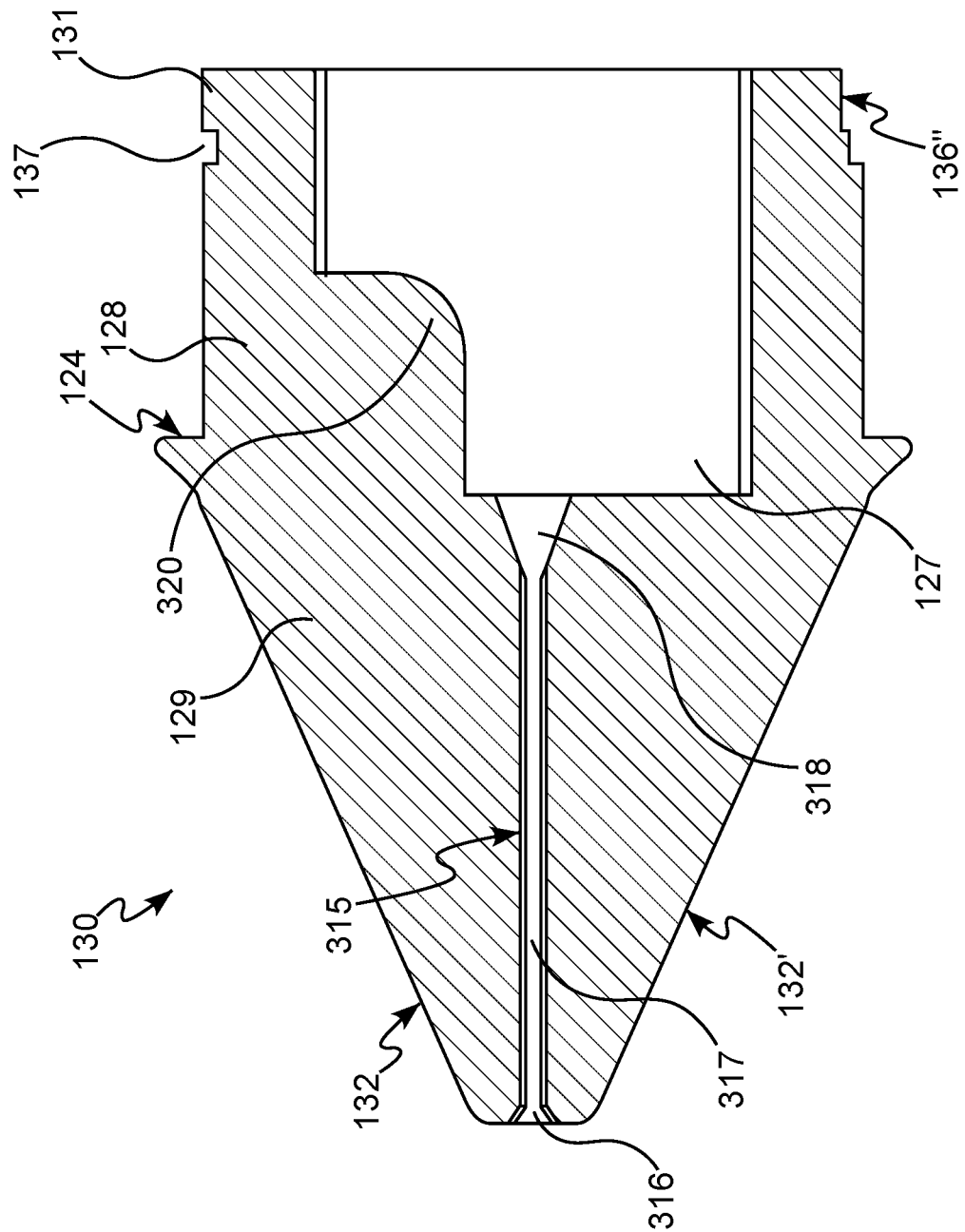
FIG. 4B is a side cross-sectional view of the nozzle of FIG. 4A.
Figure 5:
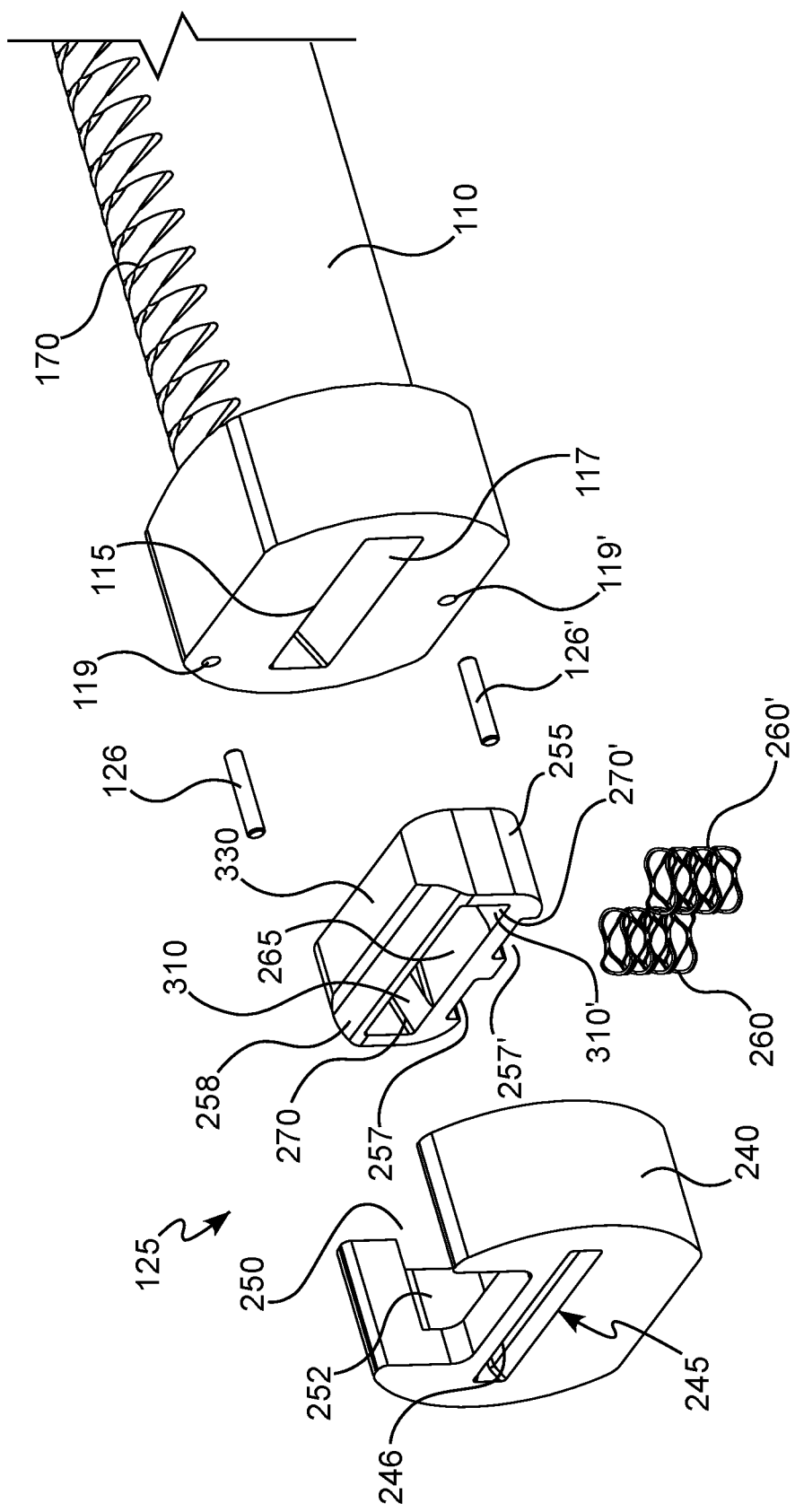
FIG. 5 is an exploded perspective view of a tool coupler of the osteotome guide of FIG. 1A.
Figure 6A:
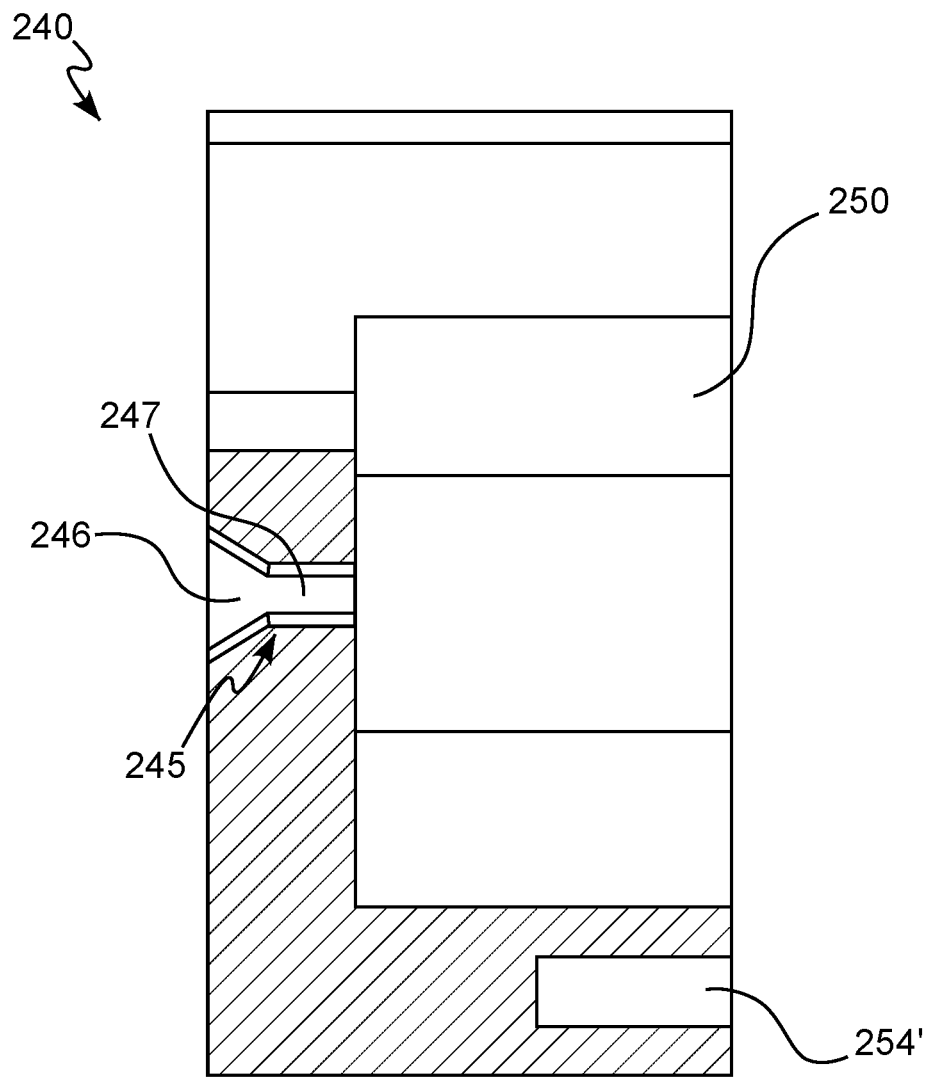
FIG. 6A is a side cross-sectional view of a tool guide of the osteotome guide of FIG. 1.
Figure 6B:
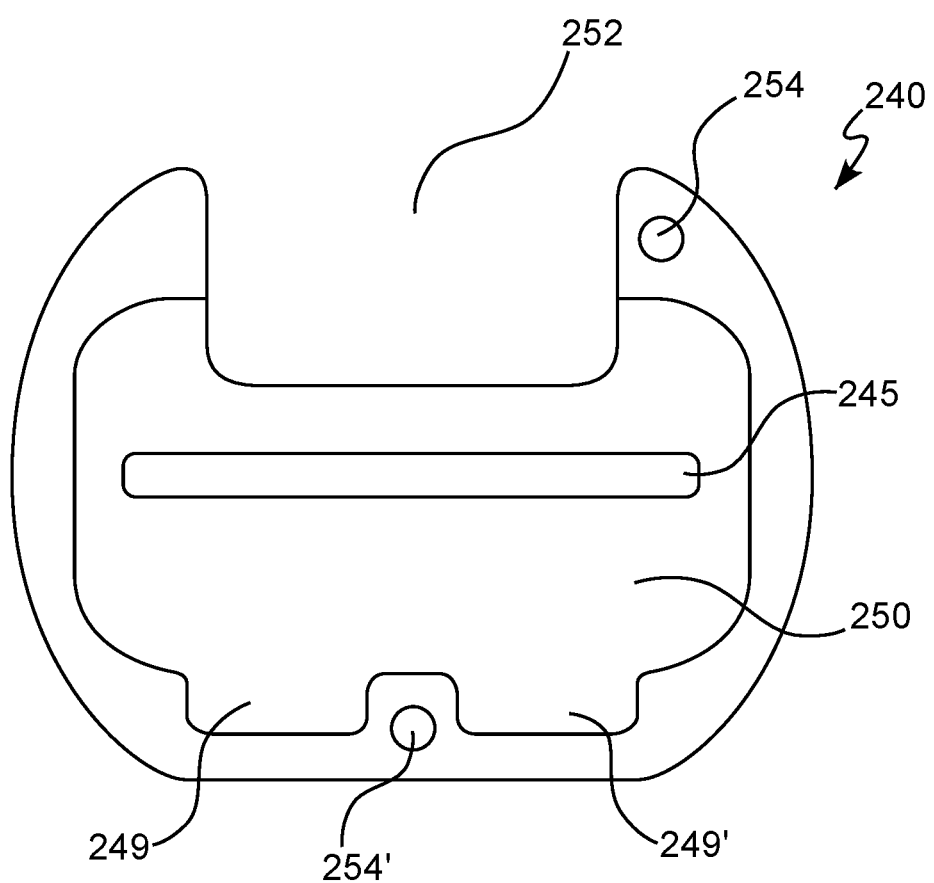
FIG. 6B is a distally facing side view of the tool guide of FIG. 6A.
Figure 7A:
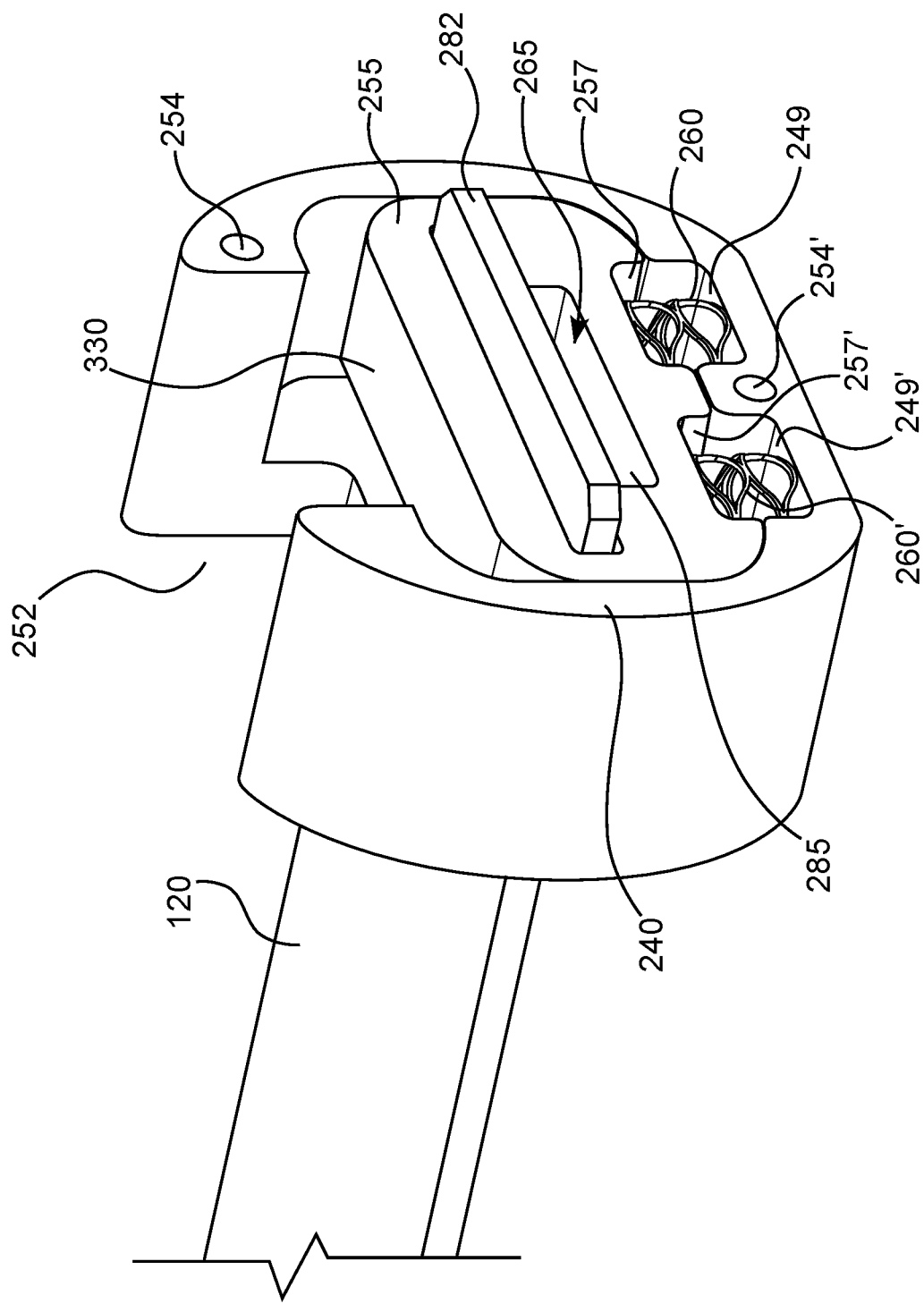
FIG. 7A is a side perspective view of the tool coupler of FIG. 5 with a partially inserted working tool.
Figure 7B:
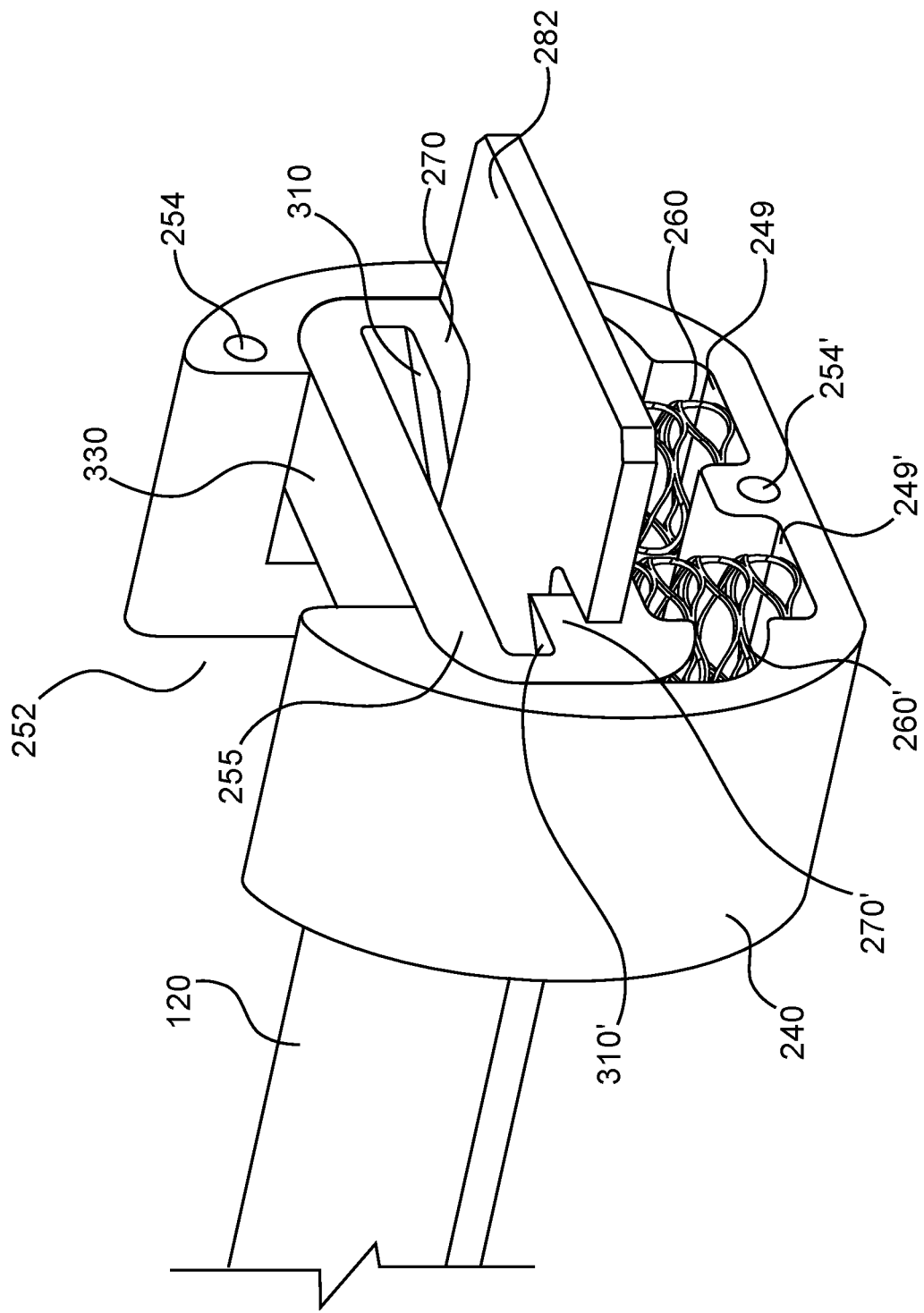
FIG. 7B is a side perspective view of the tool coupler of FIG. 5 with a fully inserted working tool.
Figure 7C:
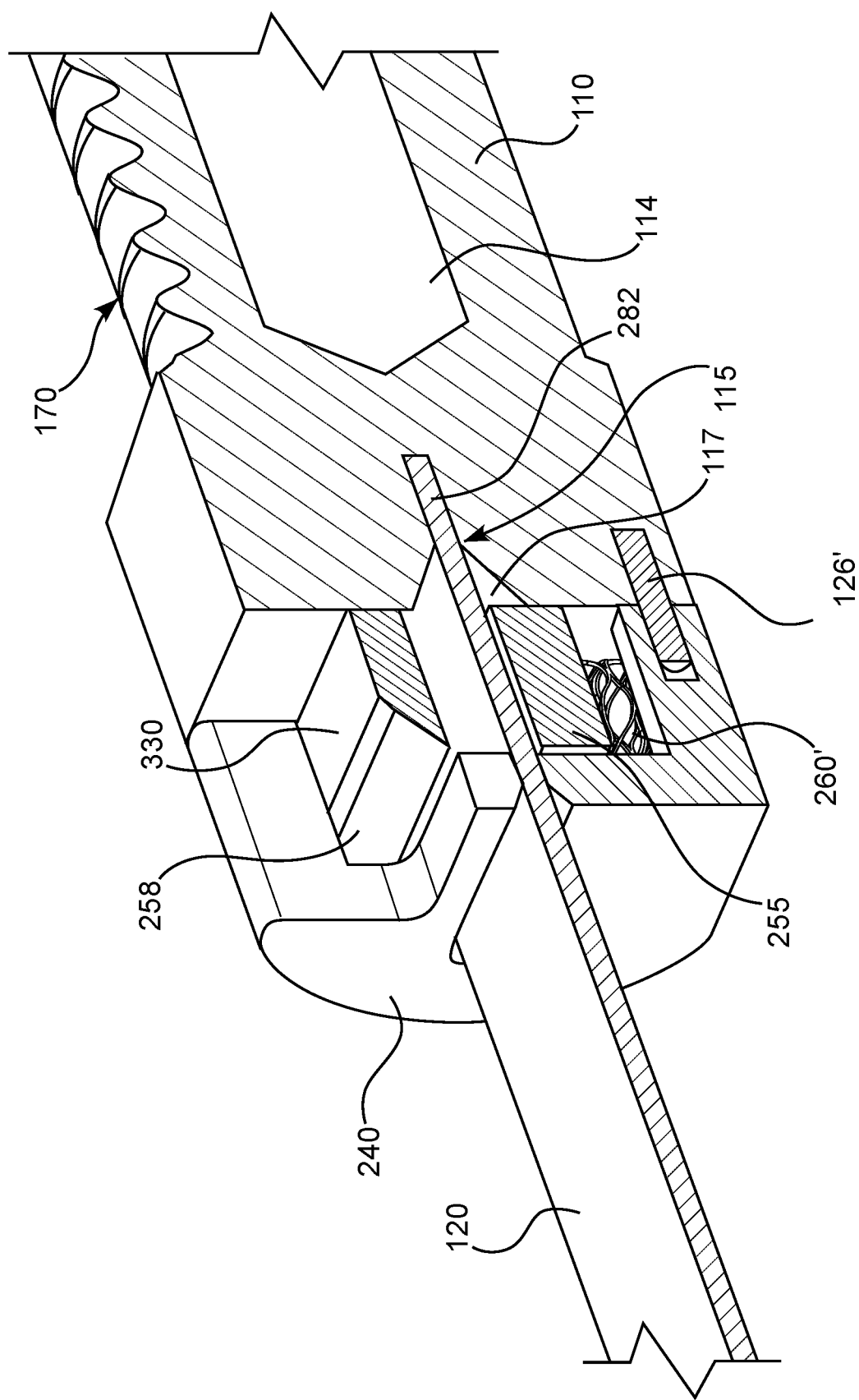
FIG. 7C is a side perspective cross-sectional view of the tool coupler of FIG. 5 attached to a guide shaft with a fully inserted working tool.
Figure 8:
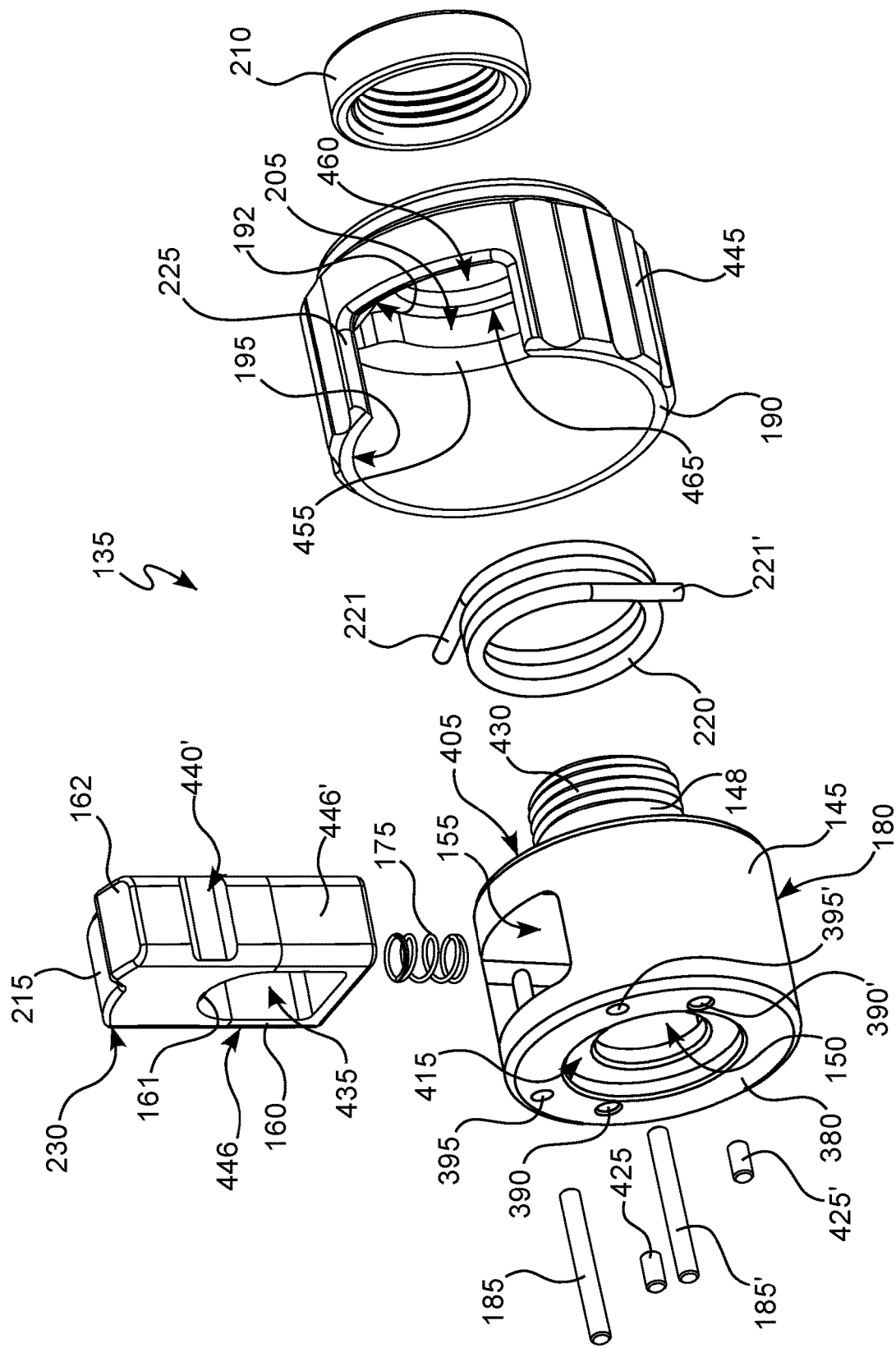
FIG. 8 is an exploded perspective view of a lock assembly of the osteotome guide of FIG. 1A.
Figure 9:
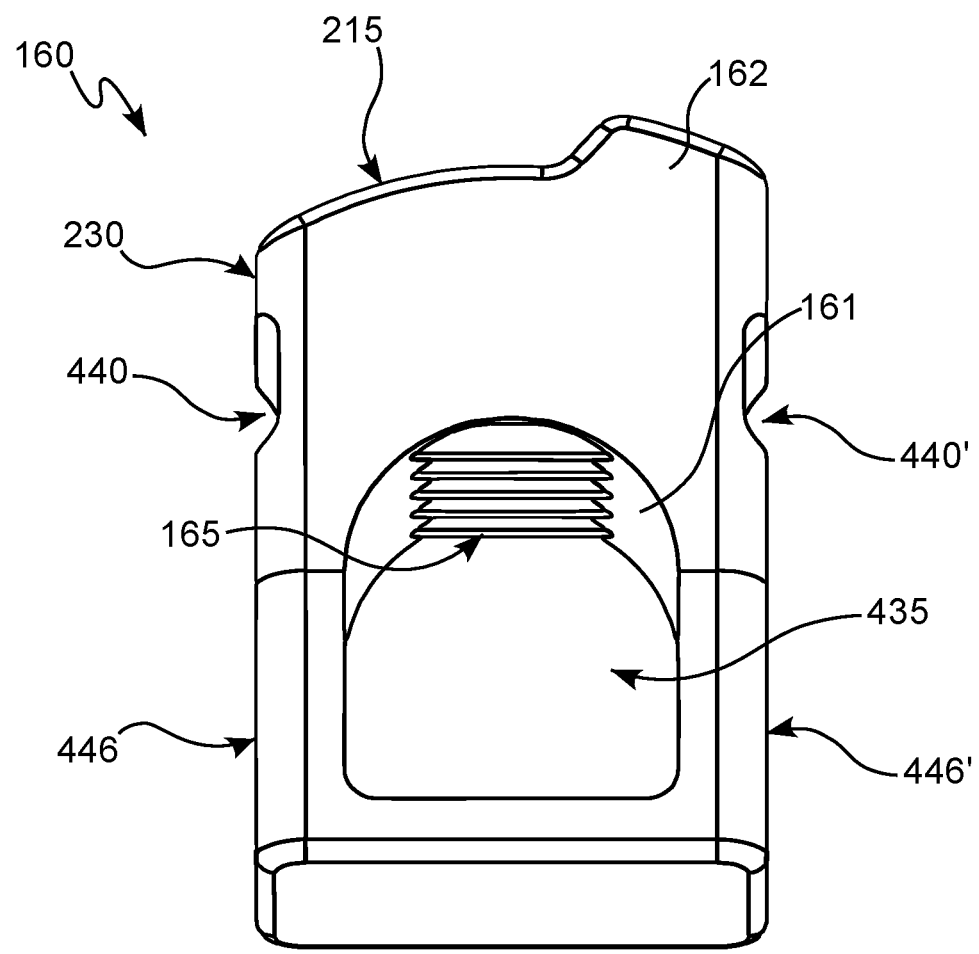
FIG. 9 is a perspective view of a clamp of the lock assembly of FIG. 8.
Figure 10:
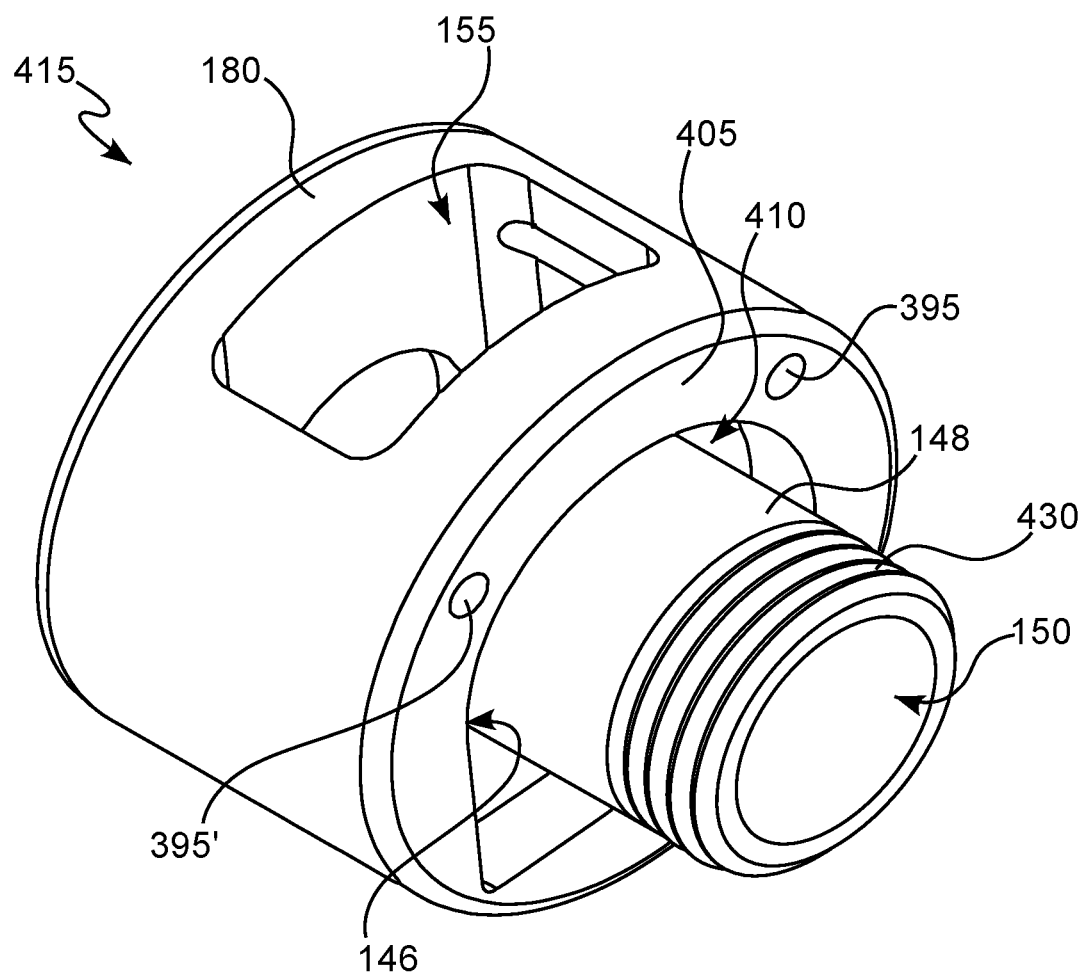
FIG. 10 is a perspective view of a housing of the lock assembly of FIG. 8.
Figure 11:
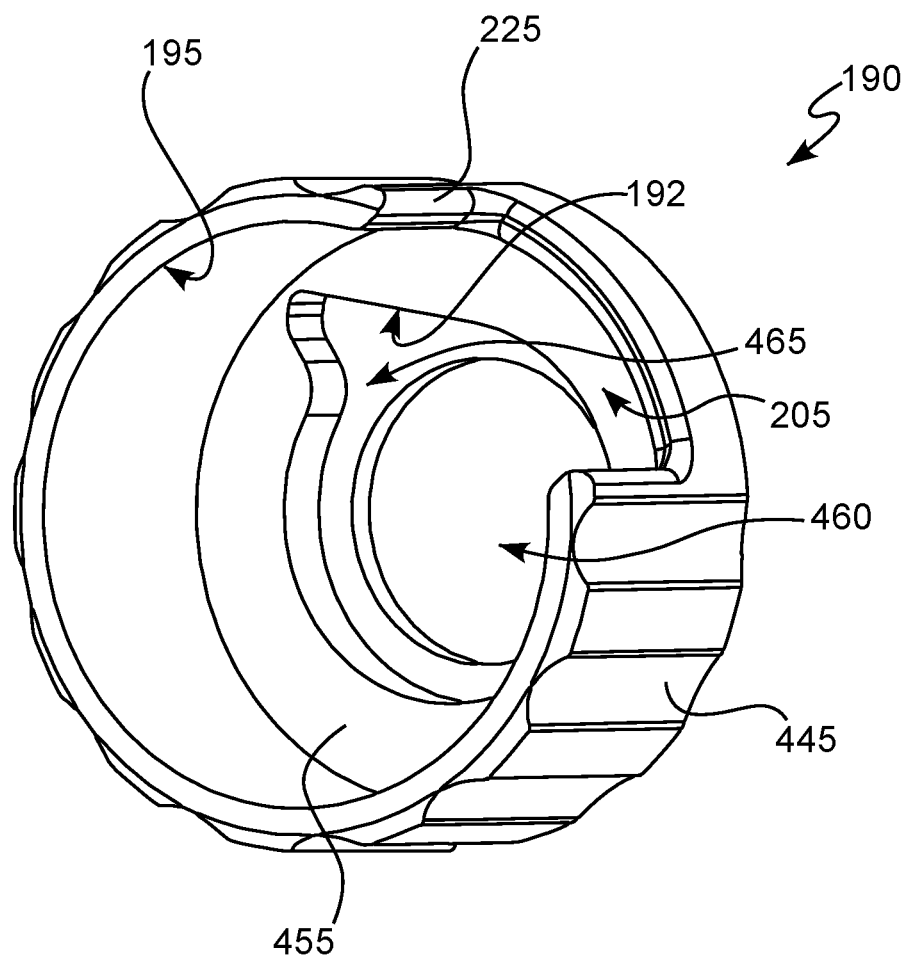
FIG. 11 is a perspective view of a collar of the lock assembly of FIG. 8.

Referring now to FIGS. 1C, 4A and 4B, the nozzle 130 encloses the tool coupler 125 and includes a cone-shaped working portion 129, a cylindrically shaped attachment portion 128 coupled integrally to the proximal end of the working portion 129, a retaining ring 295 partially circumscribing the attachment portion 128, and a threaded collar 305 circumscribing the attachment portion 128.

The cone-shaped working portion 129 of the nozzle 130 includes opposed outer tapered surfaces 132, 132' for gripping by a user and a distally facing slit 315 for receiving the working tool 120. The slit 315 is aligned with the guide slot 245 of the tool guide 240 and includes an enlarged front opening 316 tapering inwardly in the proximal direction, a mid-portion 317 in communication with the enlarged front opening 316 and an enlarged end opening 318 in communication with the mid-portion 317 and tapering outwardly in the proximal direction. The height of the mid-portion 317 of the slit 315 is approximately equal to the height of the working tool 120 to allow the slit 315 to slidably accommodate the working tool 120.

The cylindrically shaped attachment portion 128 of the nozzle 130 has a diameter less than that of the proximal end of the cone-shaped working portion 129 and, in this manner, forms a proximally facing annular ledge 124 at the boundary between the attachment and working portions 128, 129. The proximal end of the outside surface of the attachment portion 128 is provided with a circumferential groove 137 extending about the entire circumference of the attachment portion 128 and defining a circumferential lip 131 immediately proximal of the groove 137. The attachment portion 128 is also provided with a proximally facing and open internal cavity 127 in communication with the slit 315 and a curved cam protrusion 320 positioned forward of the slit 315 inside the cavity 127. The cam protrusion 320 is appropriately sized (height and width) and positioned at the front, central distal portion of the cavity 127 so as to align with and be accommodated by the front-side cutout 252 of the tool guide 240 when the shaft 110 with attached tool guide 240 is overextended distally into the nozzle 130 (see FIGS. 16A through 16C).

The circumferential lip 131 of the attachment portion 128 is sized to be accommodated within the internal pocket 109 of the handle 105 and includes cuts that form flat and radially facing surfaces 136, 136', 136" that align with the keyed surfaces 370, 370', 370" of the internal pocket 109 of the handle 105. In this manner the nozzle 130 may be properly aligned with the handle 105 before coupling the nozzle 130 thereto.

The threaded collar 305 circumscribes the attachment portion 128 proximally of the annular ledge 124 and engages with the screw threads 106 of the handle 105 for securing the nozzle 130 firmly to the handle 105. The threaded collar 305 includes an outer gripping surface 307, an annular retaining ledge 306 extending transversely and radially inward from the distal side of the gripping surface 307 and an internal surface provided with screw threads 308 opposite the gripping surface 307. The retaining ring 295 is positioned within the circumferential groove 137 of the attachment portion 128 proximally of the threaded collar 305 and engages with the annular retaining ledge 306 to maintain the threaded collar 305 on the attachment portion 128 and to prevent the collar 305 from being removed proximally therefrom. The threaded collar 305 may be unthreaded for removal of the nozzle 130 from the handle 105, thereby providing access to the tool coupler 125 and other internal components of the osteotome guide 100, such as, for example, to permit the working tool 120 to be manually removed in the event it becomes stuck within the osteotome guide 100.

Referring now to FIGS. 8-12B, the lock assembly 135 is operable to permit a user to adjust and lock the shaft 110 into a selected longitudinal position with respect to the handle 105. The lock assembly 135 includes a housing 145, a clamp 160, retaining pins 185, 185' and a biasing member 175 positioned within the housing 145, a collar 190 circumscribing and rotationally coupled to the housing 145 via a threaded cap 210, a torsion biasing element 220 (such as a torsion spring) positioned to engage the housing 145 and the collar 190, and fasteners, e.g., two fasteners 425, 425', for coupling the lock assembly 135 to the proximal end of the handle 105.

The housing 145 is generally cylindrically-shaped and includes a longitudinal bore 150 for slidably receiving the shaft 110, a circumferential outer surface 180, a distally facing attachment surface 380 transverse to the outer surface 180, an internal cavity 155 slidably receiving the clamp 160 and having an approximately rectangular cross-section and extending perpendicularly to the longitudinal bore 150 through a front-side of the outer surface 180, a blind and cylindrically-shaped receptacle 385 extending radially from a rear of the internal cavity 155 for receiving the biasing member 175, a proximally facing annular surface 405 having a pocket 410 with a first engagement face 146, and a cylindrical connector 148 with threads 430 coaxial with the longitudinal bore 150 and extending proximally from the annular surface 405.

The attachment surface 380 of the housing 145 includes two pin receipt bores 395, 395' extending proximally through the housing 145 to the annular surface 405 and communicating with the internal cavity 155, an alignment pocket 415 for receiving the cylindrical alignment member 420 of the handle 105, and distally facing fastening holes 390, 390'. The fasteners 425, 425' engage with fastening holes 390, 390' of the housing 145 and the fastening holes 103, 103' of the handle 105 to secure the lock assembly 135 to the proximal end of the handle 105. In the embodiment illustrated in the Figures, the fasteners 425, 425' are fastening pins, e.g., press-fit fastening pins, though it should be appreciated that different fasteners may be employed, such as, for example, screws, bolts, clips, etc. It should also be appreciated that the fasteners 425, 425' may be replaced by or supplemented with other structures for securing the lock assembly 135 to the handle 105, and that various embodiments of the subject disclosure are not intended to be limited to any particular number or type of structure(s) for doing so.

The clamp 160 is generally rectangular box shaped and includes a bore 435 in alignment with the longitudinal bore 150 of the housing 145, a rounded outside front surface 215, a button 162 adjacent to and extending forward of the outside front surface 215, an internal clamping surface 161 opposite the outside front surface 215 and communicating with a front side of the bore 435, locking ribs 165 provided on the internal clamping surface 161 and extending transversely to the bore 435, limiting grooves 440, 440' provided respectively on opposite lateral sides 446, 446', and a stopping surface 230 provided on the lateral side 446 above the limiting groove 440.

Figure 12A:
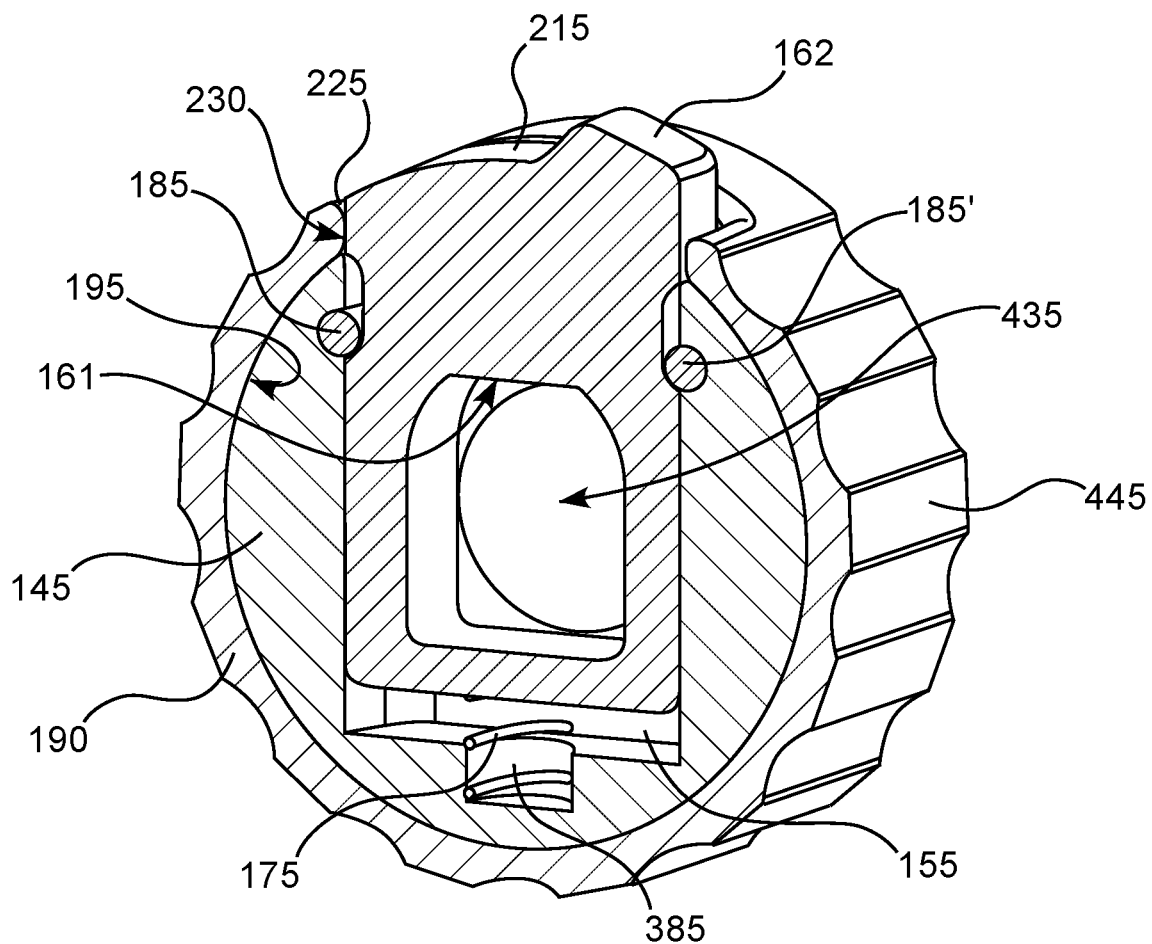
FIG. 12A is a cross-sectional perspective view of the lock assembly of FIG. 8 with the clamp in an unclamped position.

The clamp 160 is positioned to slide within the internal cavity 155 of the housing 145 between a clamped position, at which the ribs 165 engage with the locking grooves 170 of the shaft 110 to lock the shaft 110 into the selected longitudinal position with respect to the handle 105 (see FIG. 12B), and an unclamped position, at which the ribs 165 do not engage the locking grooves 170 (see FIG. 12A). The retaining pins 185, 185' extend through the pin receipt bores 395, 395' of the housing 145 and engage respectively with the limiting grooves 440, 440' of the clamp 160 to bound movement of the clamp 160 between the clamped and unclamped positions and to prevent the clamp 160 from escaping the internal cavity 155 of the housing 145.

The biasing member 175 is positioned within the receptacle 385 of the housing 145 to bias the clamp 160 into the unclamped position. In the embodiment illustrated in the Figures, the biasing member 175 is a standard compressing spring, though it should be appreciated that the biasing member 175 may be supplemented with or replaced by other structures for biasing the clamp 160, and that various embodiments of the subject disclosure are not intended to be limited to any particular number or type of biasing structure(s).

Figure 15:
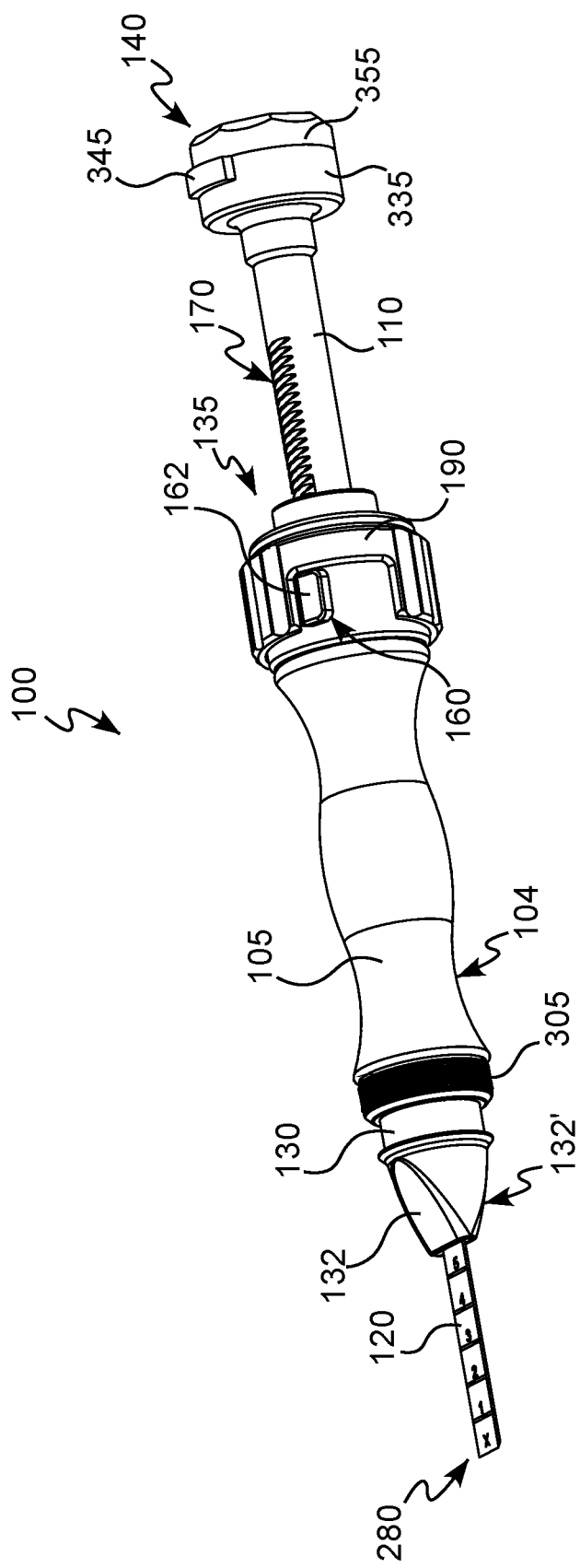
FIG. 15 is a perspective view of the osteotome guide of FIG. 1A with an attached working tool positioned and locked into an alternative longitudinal position.

The collar 190 includes a cylindrical gripping member 445 having a circumferential cutout 205, a stopping edge 225 and an inner locking surface 195, a closed proximal end 450 having a longitudinal bore 460 and an inside face 455, a pocket 465 with a second engagement face 192 on the inside face 455, and longitudinally extending grooves on an outside of the gripping member 445 to improve gripping. The longitudinal bore 460 slidably receives the cylindrical connector 148 of the housing 145 to allow the collar 190 to circumscribe and rotate freely about the housing 145 between a closed position, at which the inner locking surface 195 engages with the outside front surface 215 of the clamp 160 to maintain the clamp 160 in the clamped position (see FIGS. 12B and 15), and an open position, at which the clamp 160 extends freely through the circumferential cutout 205 (see FIGS. 1A and 12A). The threaded cap 210 engages with the threads 430 of the cylindrical connector 148 to maintain the collar 190 on the housing 145 and prevent it from being removed therefrom.

The torsion biasing element 220 is positioned within pockets 410, 465 between the housing 145 and the collar 190 and includes first and second legs 221, 221' respectively engaging the first and second engagement faces 146, 192 to bias the collar 190 into the closed position. It should be appreciated that the torsion biasing element 220 may be supplemented with or replaced by other biasing elements for biasing the collar 190 into the closed position, such as, for example, leaf springs, torsion springs, or the like, and that various embodiments of the subject disclosure are not intended to be limited to any particular number or type of biasing structure(s).

Figure 13:
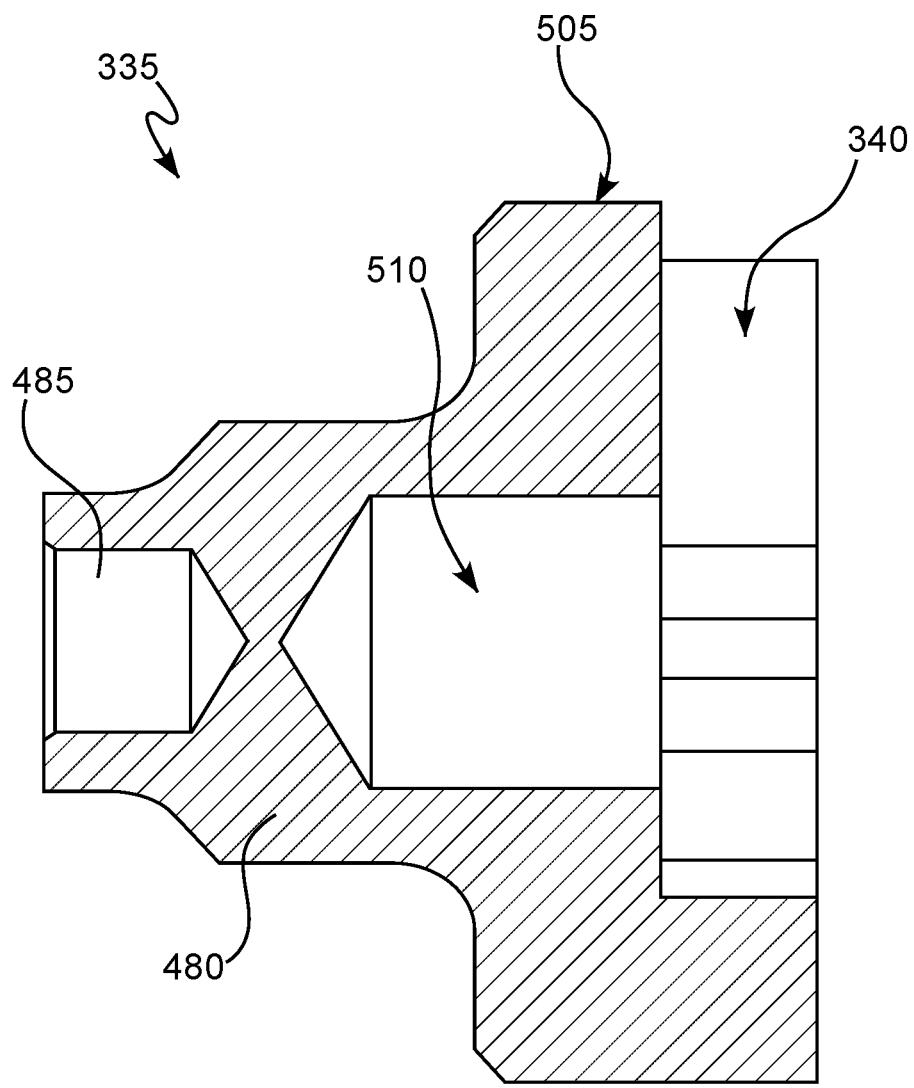
FIG. 13 is a side cross-sectional view of a housing of a securing coupler of the osteotome guide of FIG. 1A.
Figure 14A:
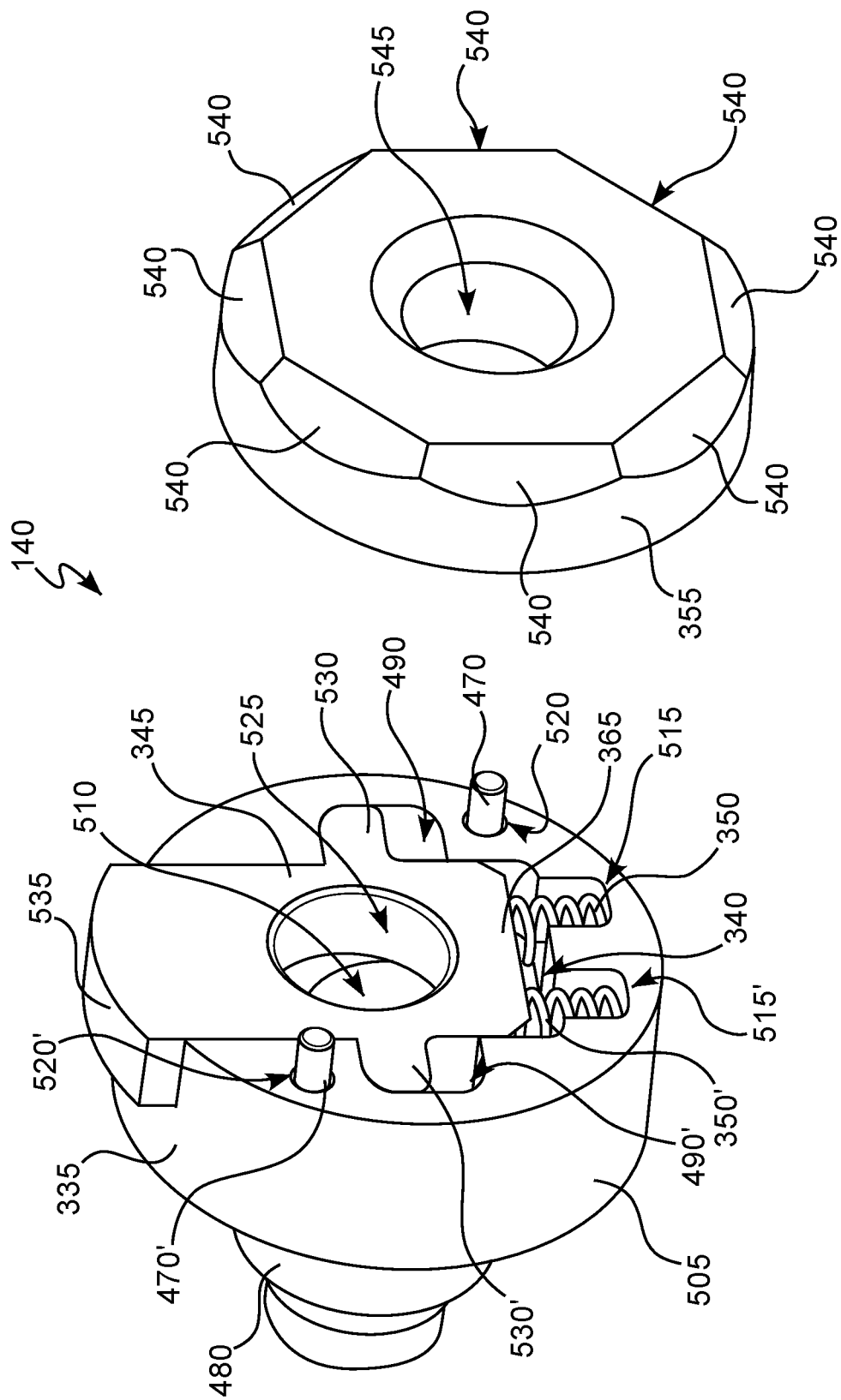
FIG. 14A is a partially exploded perspective view of a securing coupler of the osteotome guide of FIG. 1A with a locking member in a locked position.
Figure 14B:
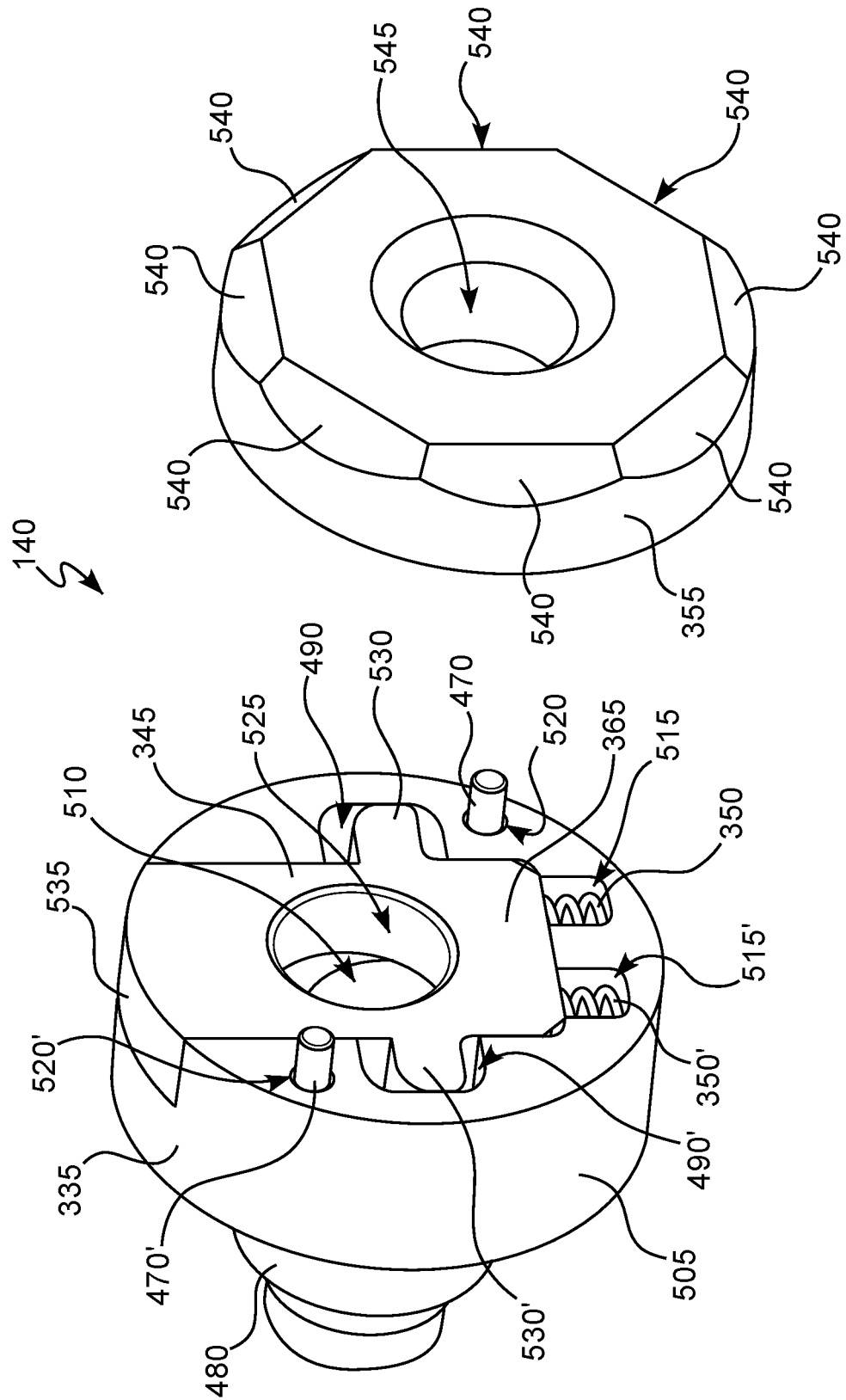
FIG. 14B is a partially exploded perspective view of a securing coupler of the osteotome guide of FIG. 1A with the locking member in an unlocked position.

Referring now to FIGS. 13 through 14B, the securing coupler 140 is operable to permit the osteotome guide 100 to be coupled to an object (not shown), such as a handle, strike plate or the like. The securing coupler 140 includes a coupler housing 335, a locking member 345 disposed within the housing 335, a cap 355 coupled to the housing 335 via fasteners, e.g., two fasteners 470, 470', and biasing members 350, 350' disposed within the housing 335 and engaging the locking member 345.

The housing 335 includes a funnel-shaped connecting portion 480 with a blind central bore 485, a cylindrically-shaped outside surface 505, an internal recess 340 extending transverse to the bore 485 and through the outside surface 505, an internal bore 510 in communication with the internal recess 340, coaxial with the blind central bore 485 and tapering to a point in a distal direction, two receptacles 515, 515' at a rear of the internal recess 340 for respectively receiving the biasing members 350, 350', diametrically opposed stopper channels 490, 490' on opposite lateral sides of the internal recess 340, and proximally facing fastening holes 520, 520'.

The locking member 345 is slidably disposed within the internal recess 340 of the housing 335 and includes a bore 525 coaxial with the internal bore 510 of the housing 335, a lower portion 365 for engaging with a groove (not shown) of the object, limiting legs 530, 530' on opposite lateral sides, and a rounded front surface 535. The locking member 345 is positioned to slide within the internal recess 340 of the housing 335 between an unlocked position, at which the lower portion 365 engages with the groove of the object to maintain and lock the object firmly to the securing coupler 140 (see FIG. 14A), and an unlocked position, at which the lower portion 365 disengages the groove of the object to permit free removal of the object from the securing coupler 140 (see FIG. 14B). The stopper channels 490, 490' of the housing 335 engage respectively with the limiting legs 530, 530' of the locking member 345 to bound movement of the locking member 345 between the locked and unlocked positions and to prevent the locking member 345 from escaping the internal recess 340 of the housing 335.

The biasing members 350, 350' are positioned respectively within the receptacles 515, 515' of the housing 335 to bias the locking member 345 into the locked position to ensure that the object is locked firmly to the securing coupler 140 while the osteotome guide 100 is in use. In the embodiment depicted in the Figures, the biasing members 350, 350' are springs, though it should be appreciated that the biasing members 350, 350' may be replaced by or supplemented with other biasing structures, and that various embodiments of the subject disclosure are not intended to be limited to any specific number or type of biasing structure(s).

The cap 355 is generally doughnut shaped and includes an outer surface with eight facets 540 (though any number of facets 540 may be provided), a central bore 545 coaxial with the internal bore 510 of the housing 335, and fastening holes (not shown) on a distally facing side. Fasteners 470, 470' engage with the fastening holes of the cap 355 and the fastening holes 520, 520' of the housing 335 to secure the cap 355 to the housing 335. In the embodiment depicted in the Figures, the fasteners 470, 470' are fastening pins, e.g., press-fit fastening pins, though it should be appreciated that different fasteners may be employed, such as, for example, screws, bolts, clips, etc. It should also be appreciated that the fasteners 470, 470' may be replaced by or supplemented with other structures for securing the cap 355 to the housing 335, and that various embodiments of the subject disclosure are not intended to be limited to any particular number or type of securing structure(s).

In operation, to lock the working tool 120 to the tool coupler 125 of the osteotome guide 100, the attachment end 282 of the working tool 120 is inserted through the slit 315 of the nozzle 130 and into the guide slot 245 of the tool guide 240. As the working tool 120 is inserted, the attachment end 282 enters the through-hole 265 of the clasp 255 and engages the ramped surfaces 310, 310' of the locking elements 270, 270', thereby causing the clasp 255 to slide transversely into the unclasped position against the biasing force produced by the biasing members 260, 260' (see FIG. 7A). Further insertion of the working tool 120 causes the attachment end 282 to clear the ramped surfaces 310, 310' and enter the shaft slot 115 of the shaft 110. As shown best in FIGS. 7B and 7C, upon full insertion of the working tool 120, the locking slots 290, 290' of the working tool 120 align respectively with the locking elements 270, 270' of the clasp 255, thereby allowing the biasing members 260, 260' to return the clasp 255 to the clasped position, at which the locking elements 270, 270' engage with the locking edges 275, 275' of the working tool 120 to lock the working tool 120 to the tool coupler 125.

Figure 16A:
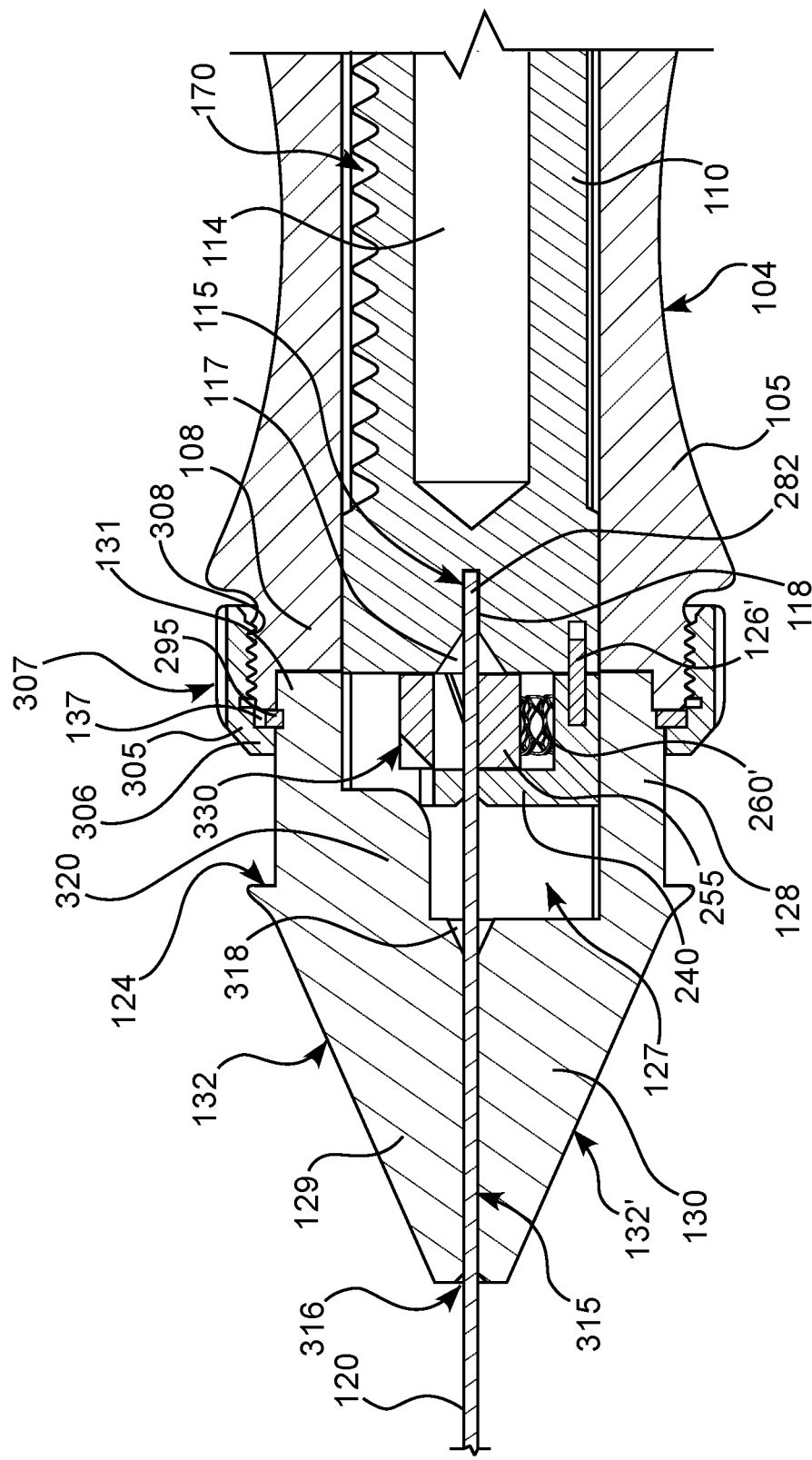
FIG. 16A is a partial side cross-sectional view of the osteotome guide and attached working tool of FIG. 1A with an internal shaft positioned into an extended position.
Figure 16B:
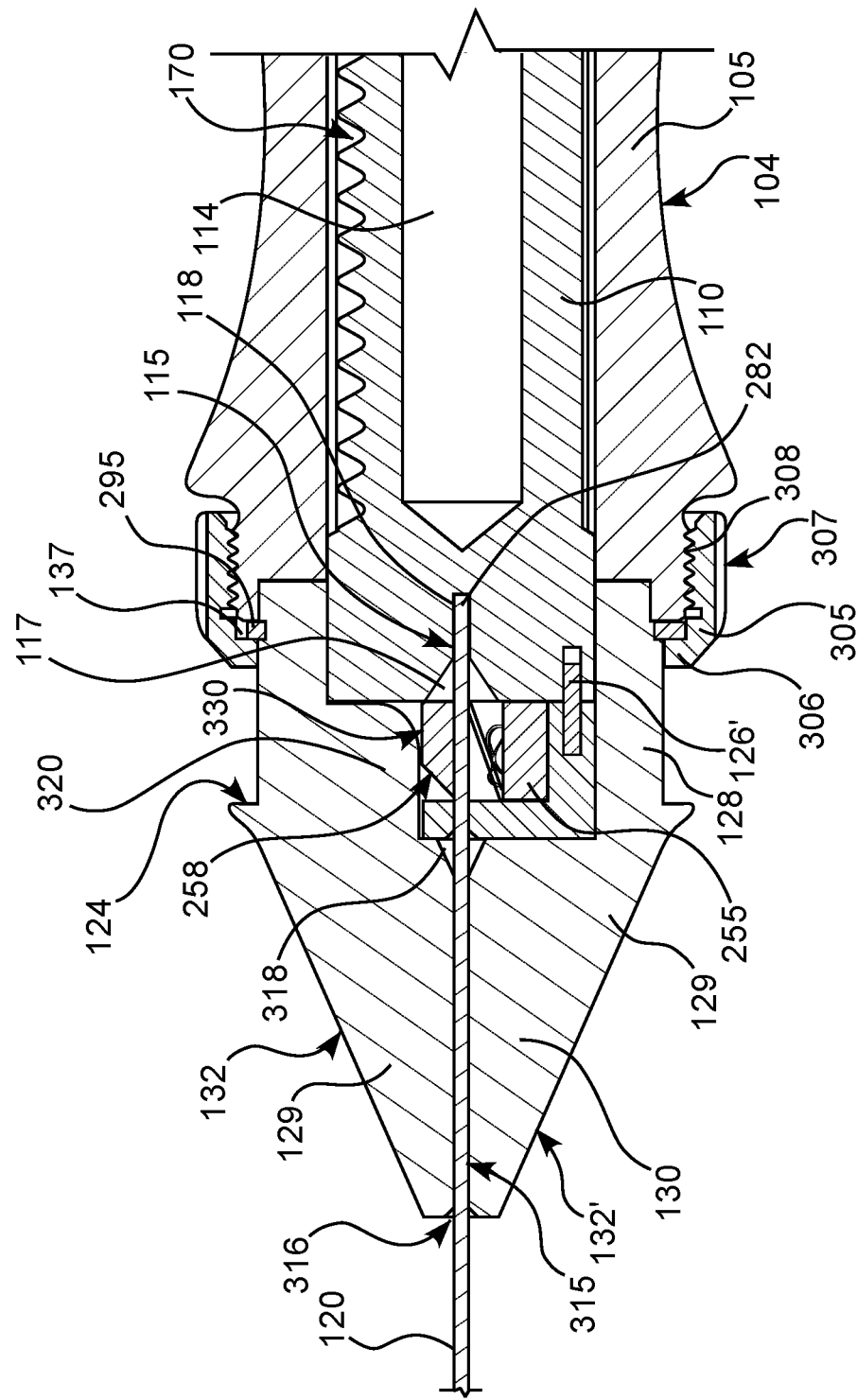
FIG. 16B is a partial side cross-sectional view of the osteotome guide and attached working tool of FIG. 1A with an internal shaft positioned into an overextended position.
Figure 16C:
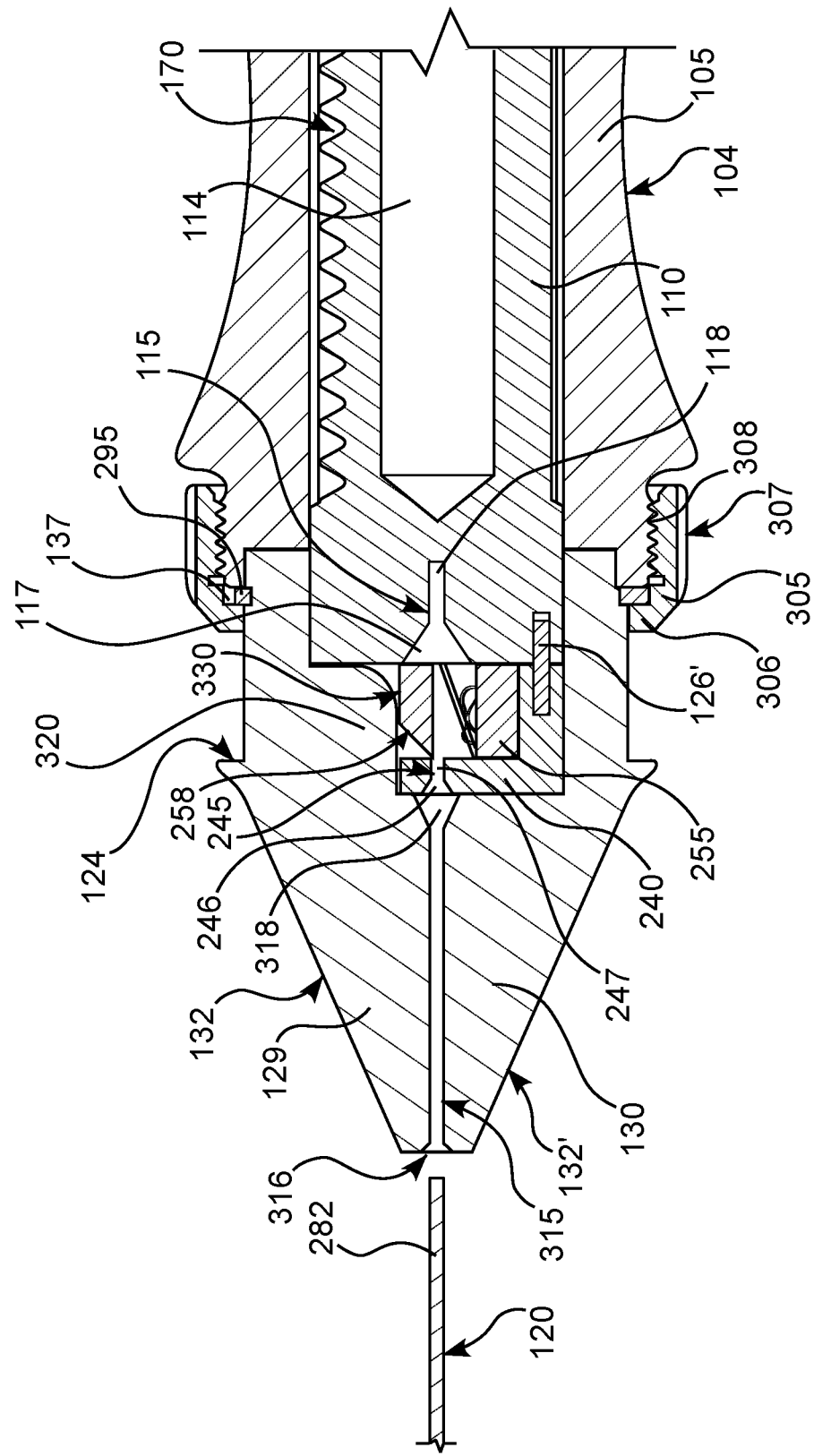
FIG. 16C is a partial side cross-sectional view of the osteotome guide of FIG. 1A with an internal shaft positioned into an overextended position and a working tool removed from the guide.

To remove the working tool 120 from the tool coupler 125, the shaft 110 is first extended distally toward the nozzle 130 until the front surface 330 of the clasp 255 engages with the cam protrusion 320 of the nozzle 130 (see FIG. 16A). As shown best in FIG. 16B, continued distal extension of the shaft 110 into an overextended position causes the cam protrusion 320 of the nozzle 130 to urge the clasp 255 into the unclasped position against the biasing force produced by the biasing members 260, 260'. This, in turn, causes the locking elements 270, 270' of the clasp 255 to disengage the locking edges 275, 275' of the working tool 120 to permit the working tool 120 to be removed longitudinally from the tool coupler 125 (see FIG. 16C).

Figure 12B:
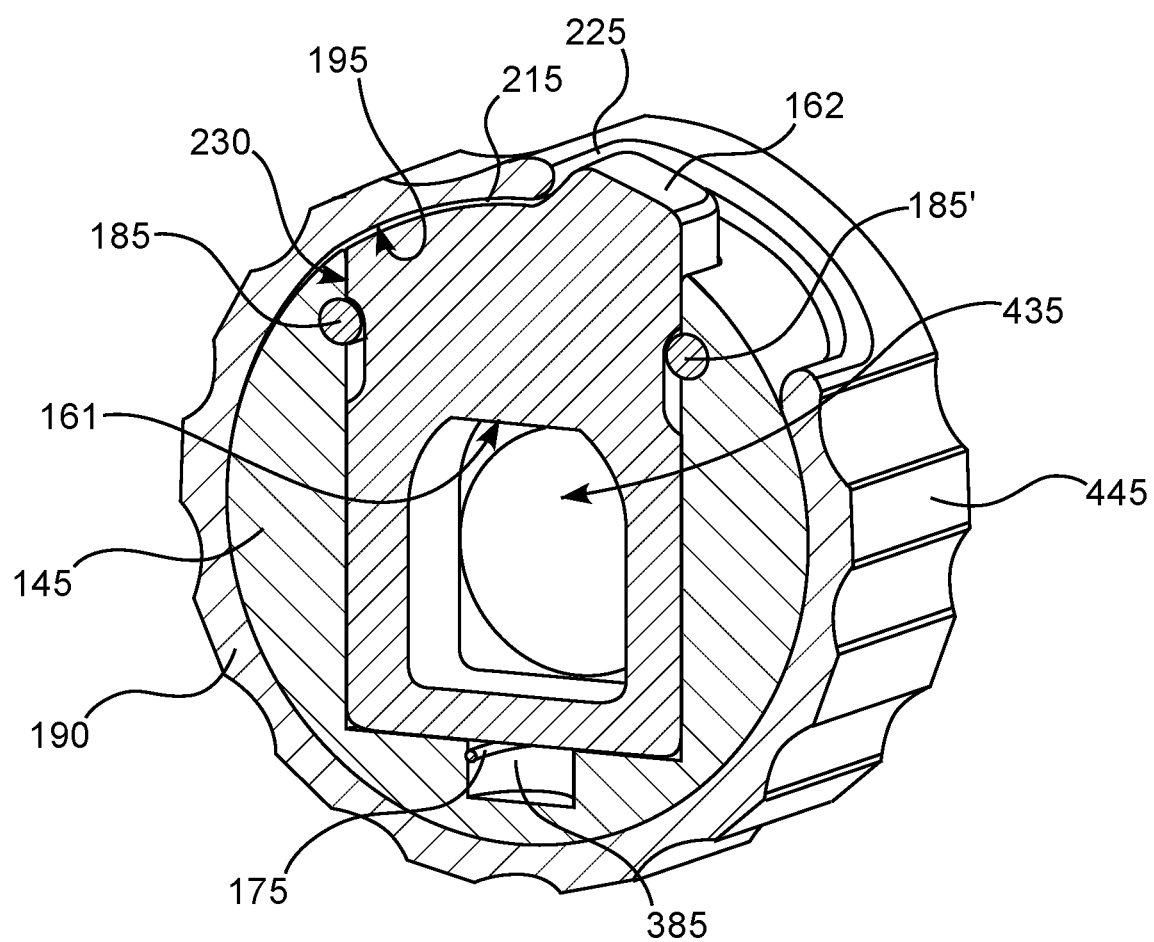
FIG. 12B is a cross-sectional perspective view of the lock assembly of FIG. 8 with the clamp in a clamped position.

As shown best in FIGS. 1A, 12A, 12B and 15, to adjust the longitudinal position of the shaft 110 with respect to the handle 105 (and thus to adjust the working tool 120 to a desired position relative to the osteotome guide 100), a user first rotates the collar 190 of the lock assembly 135 from the closed position toward the open position against the biasing force of the torsion biasing element 220. Once the collar 190 reaches the open position, the circumferential cutout 205 aligns with the clamp 160, thereby permitting the biasing member 175 to freely urge the clamp 160 from the clamped position into the unclamped position to disengage the locking ribs 165 from the locking grooves 170 of the shaft 110 (see FIG. 12A). With the clamp 160 positioned in the unclamped position, the stopping surface 230 of the clamp 160 engages the edge 225 of the collar 190 to maintain the collar 190 in the open position against the biasing force produced by the torsion biasing element 220. As shown best in FIGS. 1A and 15, the user then releases the collar 190, slides the shaft 110 manually to a selected longitudinal position and depresses the button 162 to urge the clamp 160 into the clamped position, at which the locking ribs 165 reengage the locking grooves 170 to lock the shaft 110 into the new position. As shown in FIG. 12B, urging of the clamp 160 into the clamped position also disengages the stopping surface 230 from the stopping edge 225 of the collar 190 to permit the collar 190 to return to the closed position under biasing force produced by the torsion biasing element 220. With the collar 190 in the closed position, the inner locking surface 195 of the collar 190 engages with the outside front surface 215 of the clamp 160 to maintain the clamp 160 in the clamped position. The user then releases the button 162 and operates the osteotome guide 100 as intended.

Referring again to FIGS. 14A and 14B, to lock an object (not shown) to the securing coupler 140 of the osteotome guide 100, a user first depresses the rounded front surface 535 of the locking member 345 to urge the locking member 345 into the unlocked position. The connecting end of the object is then inserted through the central bore 545 of the cap 355 until a locking groove of the object aligns with the locking member 345. Once aligned, the user releases the rounded front surface 535 of the locking member 345, causing the biasing members 350, 350' to return the locking member 345 to the locked position, at which the lower portion 365 of the locking member 345 engages with the groove of the object to lock the object to the securing coupler 140. Depressing of the rounded front surface 535 again disengages the lower portion 365 from the groove of the object to permit the object to be removed from the securing coupler 140.

The osteotome guide 100 may be used advantageously in multiple modes, for example, a first mode that may reduce undesirable buckling of the working tool 120 during a cutting operation. In the first mode, a user places collar 190 in the open position and the clamp 160 in the unclamped position, thereby permitting the shaft 110 to slide freely within and with respect to the handle 105. Next, the user slides the shaft 110 proximally to retract the working tool 120 completely within the osteotome guide 100. The most distal flat edge of the nozzle 130 is then placed against a bone to be cut, after which the user advances the working tool 120 to a desired depth with the bone by striking the most proximally facing face of the securing coupler 140 (or, in an alternative embodiment, a strike plate coupled to the securing coupler 140) with a hammer or the like. In this way, the nozzle 130 and the bone itself support the working tool 120 at all times as the tool 120 is advanced out of the osteotome guide 100 and into the bone. This may reduce undesirable buckling of working tool 120, especially in situations requiring the working tool 120 to be advanced to a large depth within the bone. Such may not be the case with respect to prior art osteotome guides that require the working tool to be advanced and locked into a particular position prior to striking, leaving much of the working tool unsupported during the cutting operation.

In a second mode of operation, the working tool 120 is first advanced out of the osteotome guide 100 and locked into a desired position relative to the guide 100 and corresponding to a particular depth marker on the working tool 120. The user then strikes the securing coupler 140 (or strike plate coupled to the securing coupler 140) to advance the working tool 120 into the bone until the most distal flat edge of the nozzle 130 contacts the bone. In this manner, the nozzle 130 operates as a hard stop to ensure that the working tool 120 is not over-inserted into the bone past the desired depth. The second mode may be particularly advantageous when cutting to shallow depths (where undesirable buckling may be less of a concern) or to ensure against accidental over-insertion of the working tool 120, such as may otherwise occur when cutting through soft bone areas.

It will be appreciated by those skilled in the art that changes could be made to the exemplary embodiments described above without departing from the broad inventive concept thereof. It is to be understood, therefore, that this disclosure is not limited to the particular embodiments disclosed, but it is intended to cover modifications within the spirit and scope of the claims defined herein.

I claim:
1. An osteotome guide comprising:
   a handle;
   a shaft within the handle and slidable to a selected longitudinal position with respect to the handle;
   a tool coupler attached to a distal end of the shaft for receiving a working tool;
   a lock assembly to lock the shaft into the selected longitudinal position with respect to the handle; and
   a securing coupler including a locking member for coupling to an object and connected to a proximal end of the shaft.
2. The osteotome guide of claim 1, wherein the handle includes a central longitudinal bore.
3. The osteotome guide of claim 1, wherein the handle includes screw threads about its distal end for coupling to a threaded collar.
4. The osteotome guide of claim 1, wherein the shaft is elongated.
5. The osteotome guide of claim 1, wherein the shaft includes a plurality of grooves.
6. The osteotome guide of claim 1, wherein the shaft includes a distal end having a shaft slot for receiving the working tool.
7. The osteotome guide of claim 1, wherein the tool coupler includes a tool guide having an internal cavity and a clasp positioned within the internal cavity.
8. The osteotome guide of claim 7, wherein the clasp is positionable between a clasped position and an unclasped position.

9. The osteotome guide of claim 8, wherein the tool coupler further includes a biasing member to bias the clasp into the clasped position.

10. The osteotome guide of claim 1, wherein the lock assembly comprises:
   a housing; and
   a clamp mounted within and moveable relative to the housing between a clamped position and an unclamped position, wherein in the clamped position the clamp engages the shaft to lock the shaft into the selected longitudinal position.

11. The osteotome guide of claim 10, wherein the clamp includes an inner locking surface for engaging the shaft when the clamp is in the clamped position.

12. The osteotome guide of claim 11, wherein the inner locking surface of the clamp includes a plurality of locking ribs.

13. The osteotome guide of claim 10, wherein the clamp includes a biasing member to bias the clamp into the unclamped position.

14. The osteotome guide of claim 10, wherein the lock assembly further includes a collar circumscribing the housing and rotatable about the housing between locked and unlocked positions, wherein the collar maintains the clamp in the clamped position when the collar is positioned into the locked position.

15. The osteotome guide of claim 14, wherein the clamp further includes a button extending past the collar and being manually manipulatable to urge the clamp into the clamped position.

16. The osteotome guide of claim 1, further comprising a nozzle coupled to the handle.

17. The osteotome guide of claim 16, wherein the nozzle includes a slit for receiving the working tool.

18. The osteotome guide of claim 16, further comprising a threaded collar structured to couple the nozzle to the handle.

19. A method of operating the osteotome guide of claim 1, the method comprising:
   attaching the working tool to the tool coupler;
   retracting the working tool into the handle; and
   striking the securing coupler to advance the working tool into a bone without first operating the lock assembly to lock the shaft into the selected longitudinal position with respect to the handle.

20. The method of claim 19, wherein the step of striking the securing coupler includes striking a strike plate coupled to the securing coupler.

21. A method of operating the osteotome guide of claim 1, the method comprising:
   attaching the working tool to the tool coupler;
   positioning the shaft into the selected longitudinal position with respect to the handle, thereby positioning the working tool to a desired position with respect to the nozzle;
   operating the lock assembly to lock the shaft into the selected longitudinal position with respect to the handle; and
   striking the securing coupler to advance the working tool into a bone until the nozzle contacts the bone.

22. The method of claim 21, wherein the step of striking the securing coupler includes striking a strike plate coupled to the securing coupler.

23. A osteotome guide for accommodating an osteotome blade, comprising:
   a handle having a longitudinal bore;
   a guide shaft having a distal end, a proximal end, and an outer surface provided with a plurality of grooves; the guide shaft disposed within the bore of the handle and slidable to a selected longitudinal position with respect to the handle;
   a tool coupler attached to the distal end of the guide shaft to removably receive the osteotome blade, the tool coupler including a clasp positionable into a locked position to lock the osteotome blade to the guide shaft and an unlocked position to unlock the osteotome blade from the guide shaft and a biasing member biasing the clasp into the locked position;
   a tapered nozzle having a slit for receiving the osteotome blade and an inner surface provided with a detent, the nozzle coupled to a distal end of the handle and engageable with the clasp of the tool coupler when the shaft is positioned into an overextended position;
   a lock assembly including:
      a housing having;
      a clamp positioned within the housing and having a stopping surface, an outside surface, a button adjacent to the outside surface and an internal clamping surface provided with a plurality of locking ribs, the clamp being positionable into a clamped position and an unclamped position, the locking ribs engaging the grooves of the guide shaft in the clamped position to lock the guide shaft into the selected longitudinal position, the button being manually manipulatable to urge the clamp into the clamped position,
      a toggle spring to bias the clamp into the unclamped position,
      a collar circumscribing the clamp and having an inner surface, the collar being rotatable into a closed position and an open position, the inner surface of the collar maintaining the clamp in the clamped position when the collar is rotated into the closed position, the stopping surface of the clamp engaging with the collar when the clamp is in the unclamped position to prevent the collar from being rotated from the open position to the closed position, and
      a torsion spring to bias the collar into the closed position; and
   a securing coupler connected to the proximal end of the guide shaft to couple the guide shaft to an object.

* * * * *